(12) United States Patent
Yuasa et al.

(10) Patent No.: US 11,622,765 B2
(45) Date of Patent: Apr. 11, 2023

(54) CLIPPING DEVICE FOR LARGE DEFECTS, PERFORATIONS AND FISTULAS

(71) Applicant: OLYMPUS CORPORATION, Hachioji (JP)

(72) Inventors: Masaru Yuasa, Hachioji (JP); Yoshisane Nakamura, Hachioji (JP); David Andrew Desmarais, Seattle, WA (US); Adam L Smith, Palm Desert, CA (US); Amanda Kay Woodcock, Seattle, WA (US); Donald C. Baumgarten, Seattle, WA (US)

(73) Assignee: OLYMPUS CORPORATION, Tokyo (JP)

( * ) Notice: Subject to any disclaimer, the term of this patent is extended or adjusted under 35 U.S.C. 154(b) by 122 days.

(21) Appl. No.: 16/709,328

(22) Filed: Dec. 10, 2019

(65) Prior Publication Data
US 2020/0214705 A1    Jul. 9, 2020

Related U.S. Application Data

(60) Provisional application No. 62/787,787, filed on Jan. 3, 2019.

(51) Int. Cl.
*A61B 17/08* (2006.01)
*A61B 17/12* (2006.01)
*A61B 17/11* (2006.01)

(52) U.S. Cl.
CPC ...... *A61B 17/083* (2013.01); *A61B 17/12031* (2013.01); *A61B 2017/1125* (2013.01); *A61B 2017/1205* (2013.01)

(58) Field of Classification Search
CPC .......... A61B 2017/1125; A61B 17/083; A61B 17/12031; A61B 2017/12054–12095;
(Continued)

(56) References Cited

U.S. PATENT DOCUMENTS

2005/0107809 A1    5/2005  Litscher et al.
2005/0251189 A1    11/2005 Saadat et al.
(Continued)

FOREIGN PATENT DOCUMENTS

EP    1547529 A1    6/2005
EP    3081174 A1    10/2016
(Continued)

OTHER PUBLICATIONS

Jun. 16, 2021 International Preliminary Report on Patentability issued in International Patent Application No. PCT/IB2019/001322.
(Continued)

*Primary Examiner* — Sarah A Simpson
*Assistant Examiner* — Raihan R Khandker
(74) *Attorney, Agent, or Firm* — Oliff PLC

(57) ABSTRACT

A tissue clipping device and system, and method for clipping tissue are disclosed. The tissue clipping device includes a clip with clip arms that is slidably disposed within a channel of a lock tube. The clip is designed to move between an open configuration in which distal ends of the clip arms are separated from each other for receiving tissue therebetween, and a closed configuration in which the distal ends of the clip arms are closer to each other than in the open configuration for clipping the tissue received therebetween. The tissue clipping system further includes a delivery device for delivering and deploying the tissue clipping device. The delivery device is releasably coupled to the tissue clipping device.

25 Claims, 40 Drawing Sheets

(58) Field of Classification Search
CPC ........... A61B 2017/00632; A61B 2017/00584;
A61B 2017/00606; A61B 2017/00615;
A61B 17/08; A61B 17/1227; A61B
17/128; A61B 17/1285
See application file for complete search history.

(56) References Cited

U.S. PATENT DOCUMENTS

| | | | | |
|---|---|---|---|---|
| 2005/0251202 | A1* | 11/2005 | Ewers | A61B 17/0401 |
| | | | | 606/213 |
| 2006/0271072 | A1* | 11/2006 | Hummel | A61B 17/1285 |
| | | | | 606/142 |
| 2011/0245855 | A1* | 10/2011 | Matsuoka | A61B 17/122 |
| | | | | 606/157 |
| 2013/0226200 | A1* | 8/2013 | Kappel | A61B 17/122 |
| | | | | 606/142 |
| 2014/0171973 | A1 | 6/2014 | Zhu | |
| 2014/0171974 | A1 | 6/2014 | Zhu | |
| 2014/0379018 | A1 | 12/2014 | Martinez et al. | |
| 2016/0242778 | A1 | 8/2016 | Xu et al. | |
| 2016/0367258 | A1 | 12/2016 | Jin et al. | |
| 2017/0119398 | A1 | 5/2017 | Kappel et al. | |
| 2018/0140300 | A1 | 5/2018 | Randhawa | |
| 2019/0150929 | A1* | 5/2019 | Gregan | A61B 17/1285 |

FOREIGN PATENT DOCUMENTS

| | | |
|---|---|---|
| JP | 2004-073646 A | 3/2004 |
| JP | 2006-198388 A | 8/2006 |
| JP | 2016-526448 A | 9/2016 |
| JP | 2017-509392 A | 4/2017 |
| JP | 2019-524351 A | 9/2019 |
| WO | 2004/017839 A1 | 3/2004 |
| WO | 2009/155286 A1 | 12/2009 |
| WO | 2015/006083 A1 | 1/2015 |
| WO | 2018/097972 A1 | 5/2018 |

OTHER PUBLICATIONS

Sep. 6, 2022 Office Action issued in Japanese Patent Application No. 2021-539086.

* cited by examiner

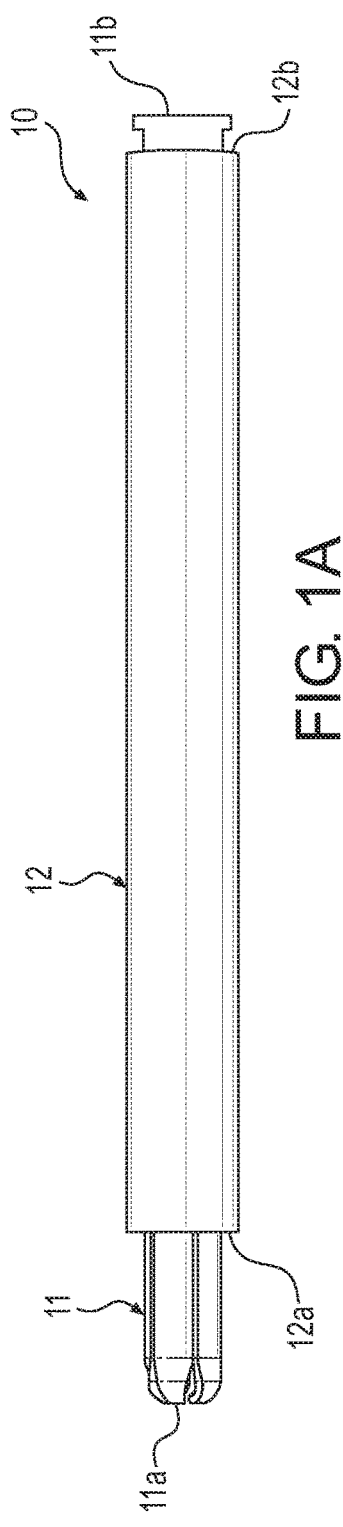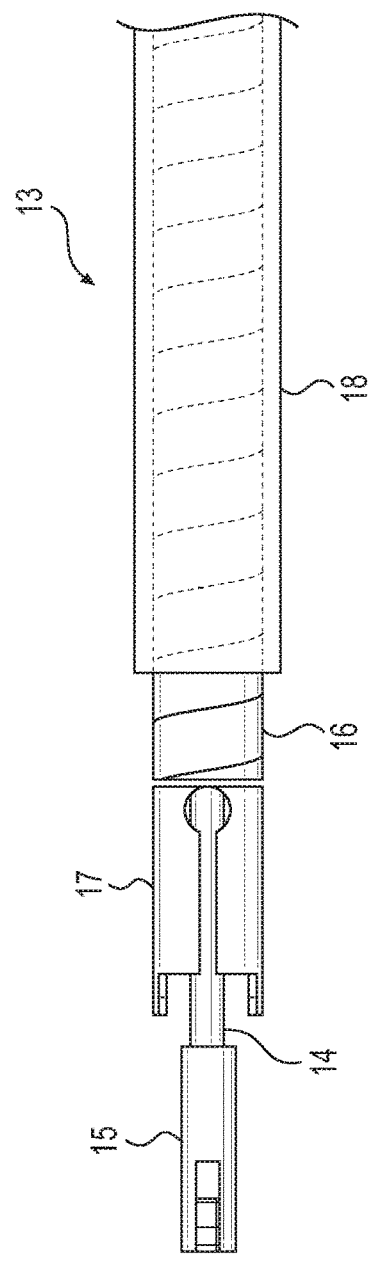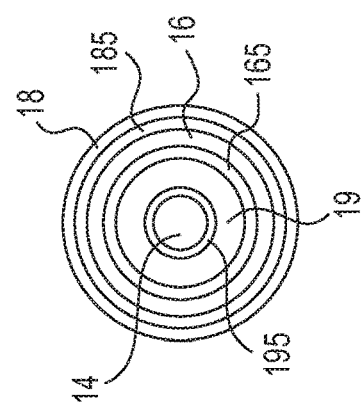
FIG. 1A
FIG. 1C
FIG. 1B

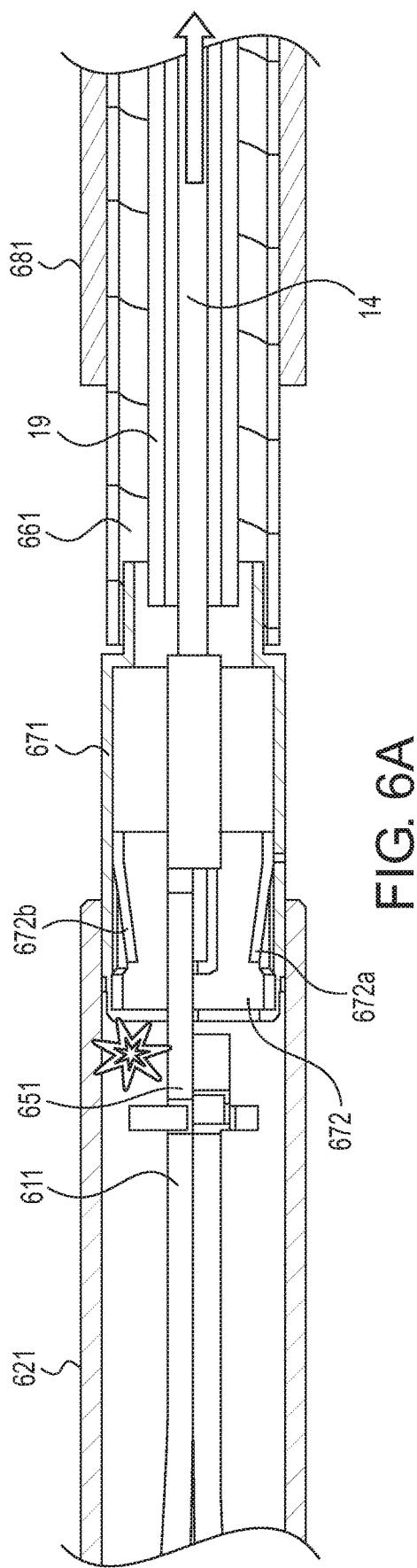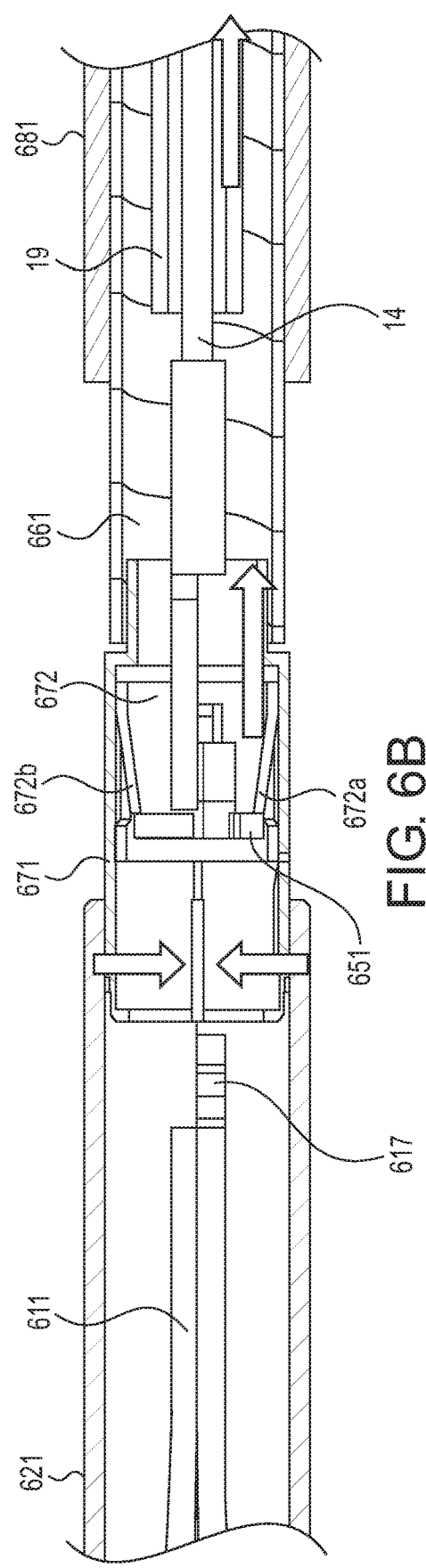

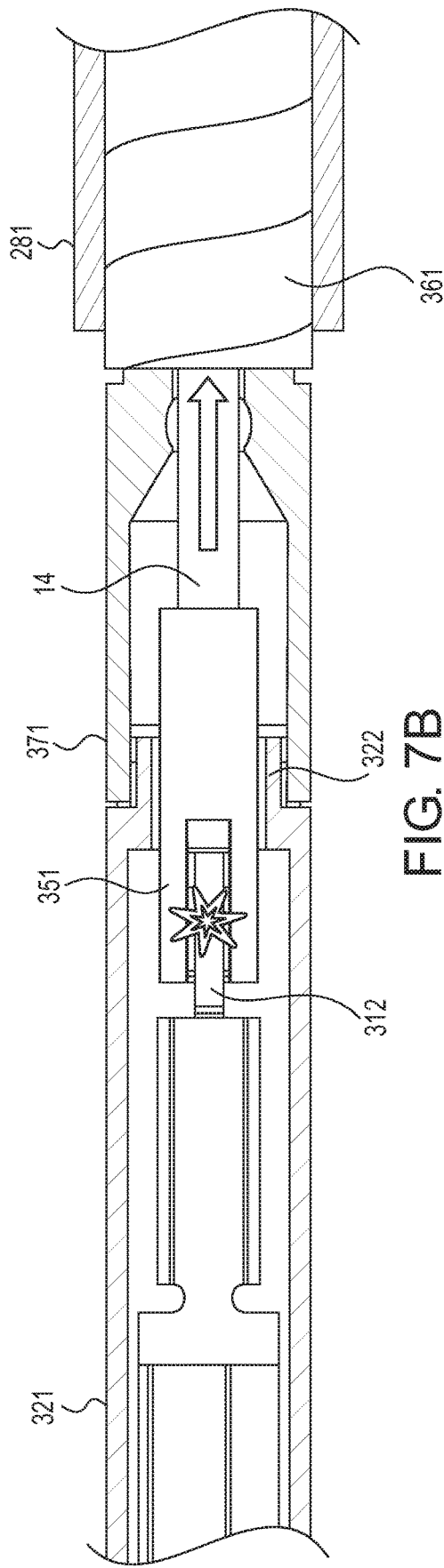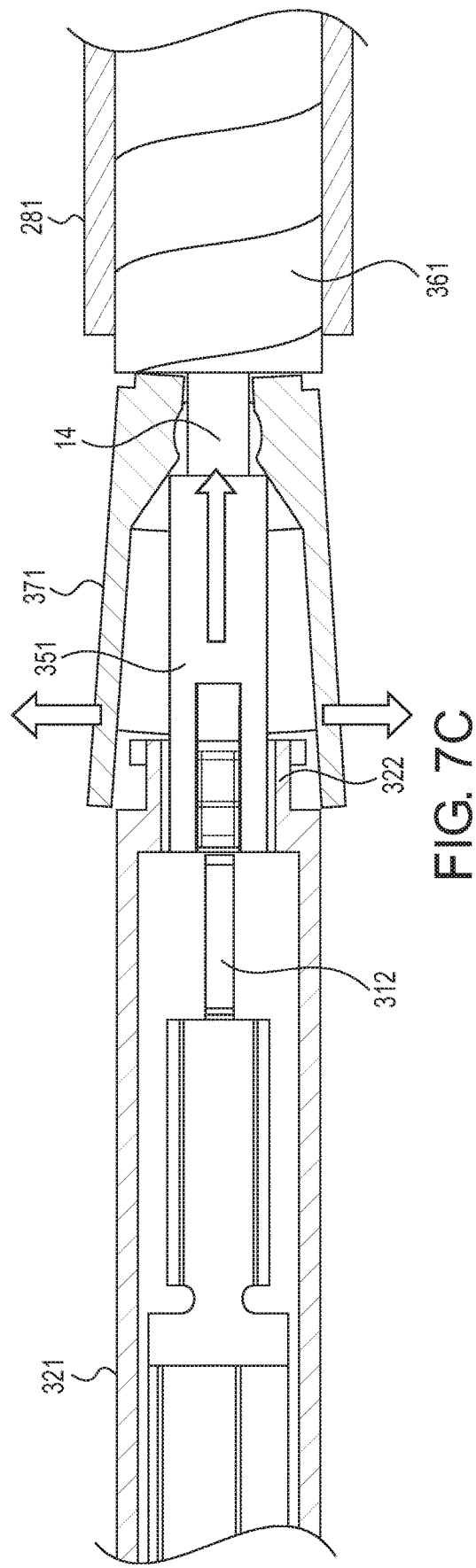

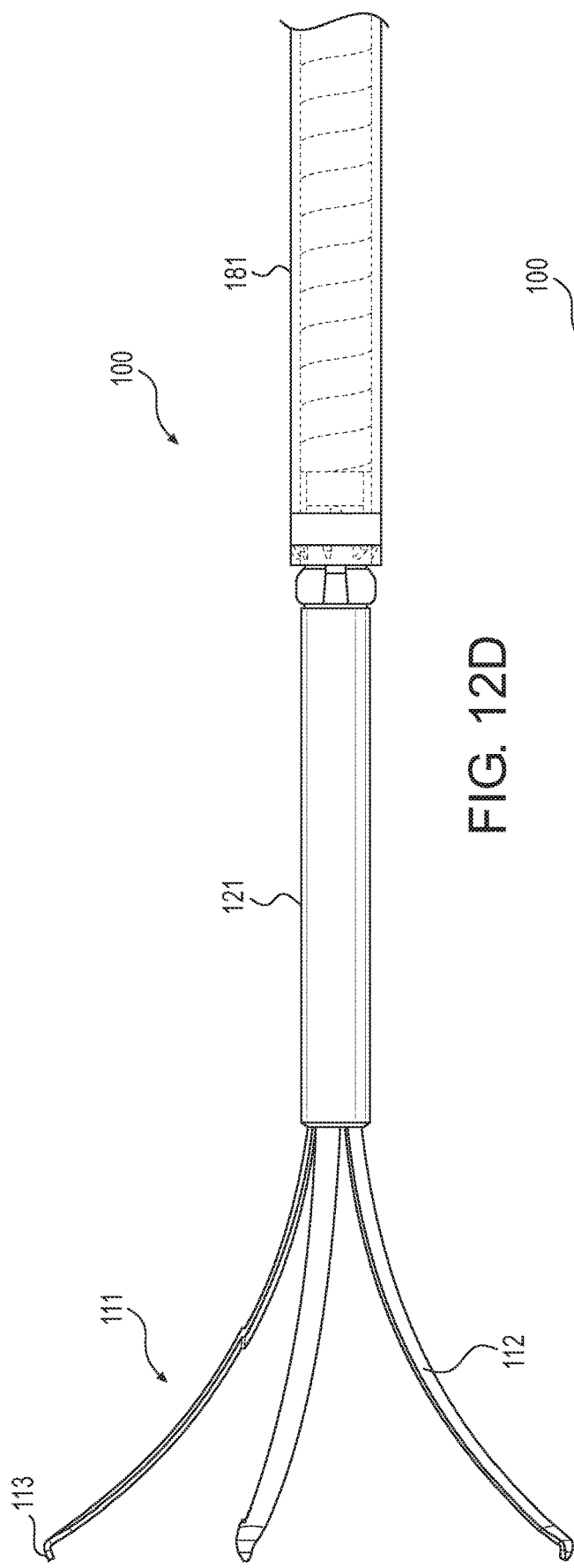
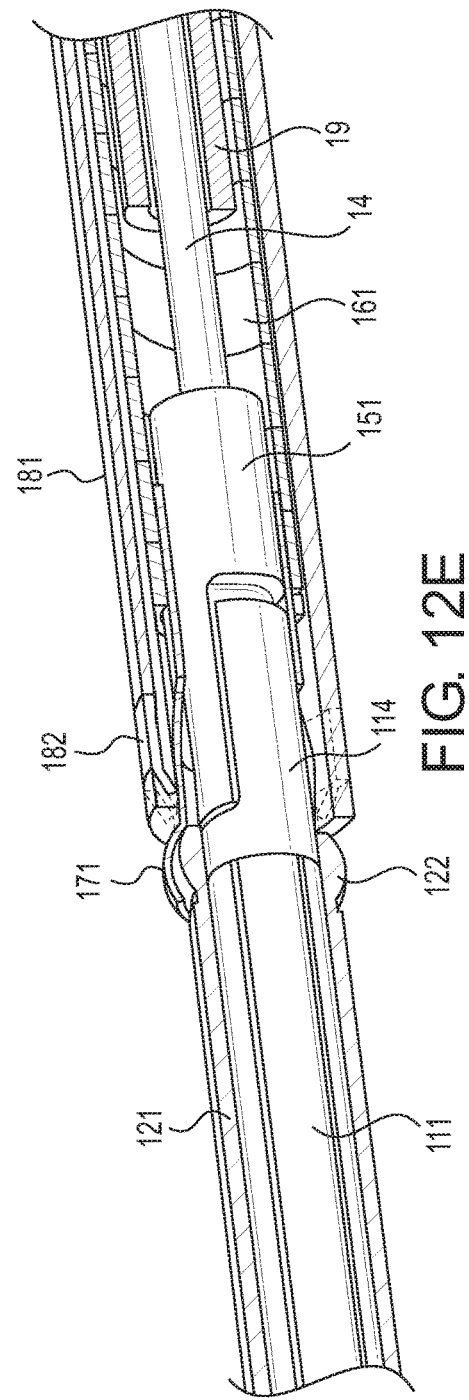
FIG. 12D
FIG. 12E

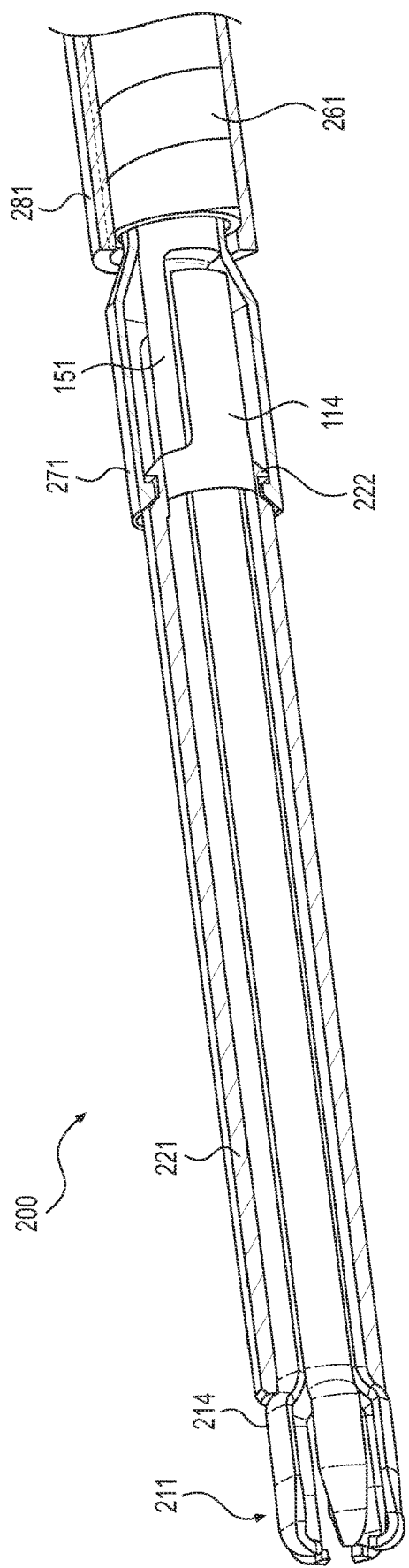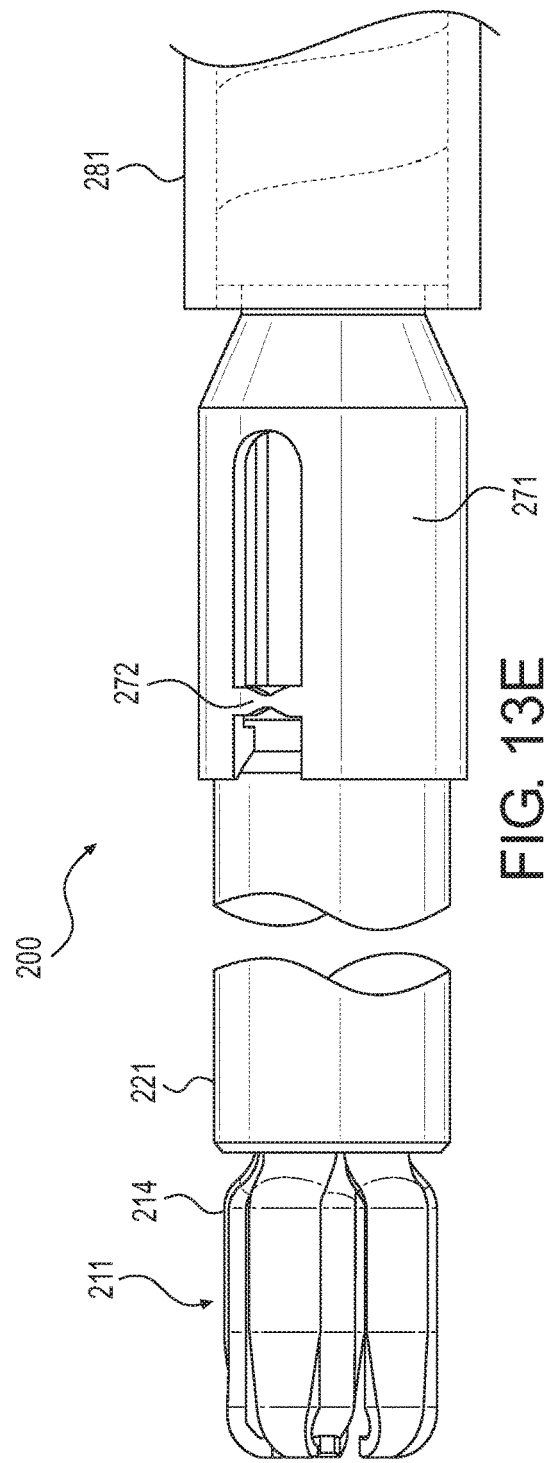
FIG. 13D
FIG. 13E

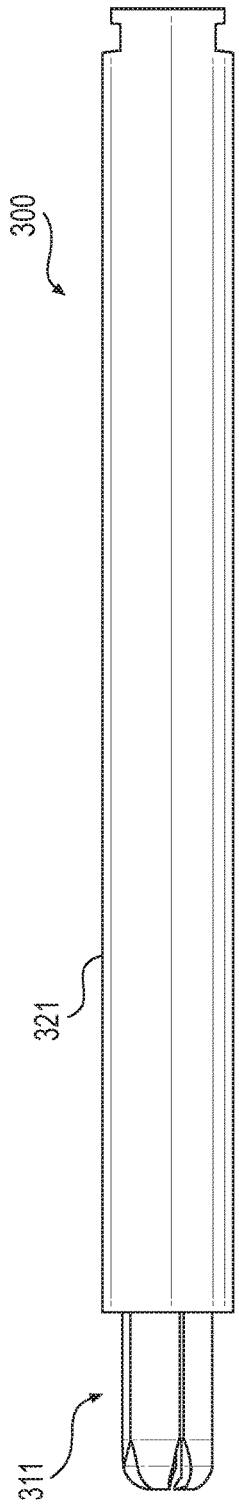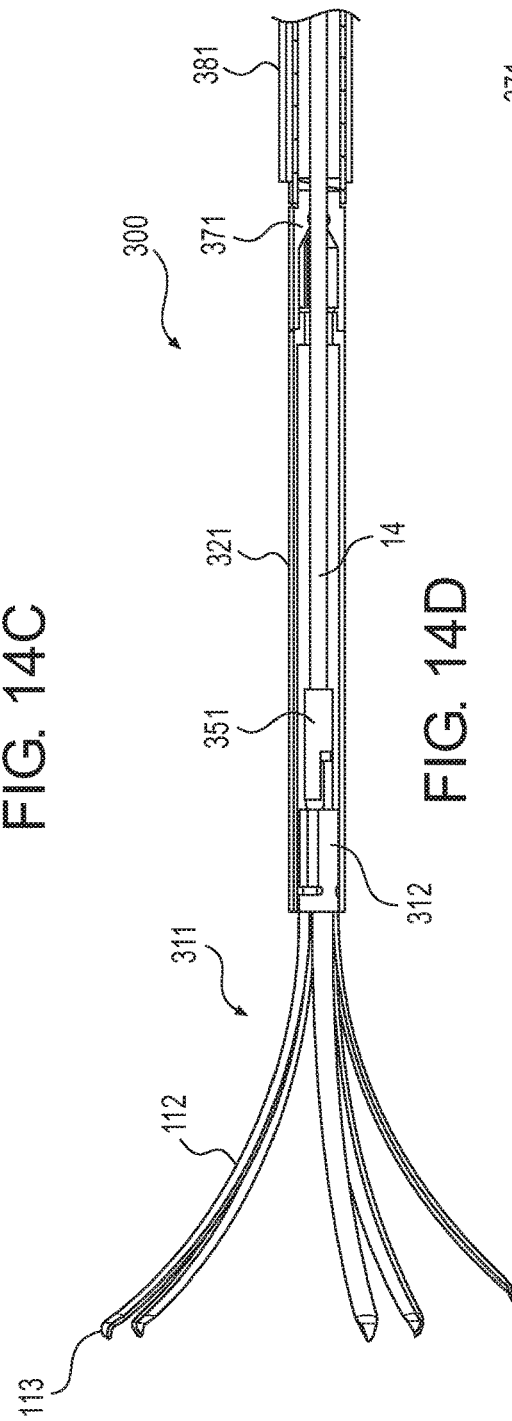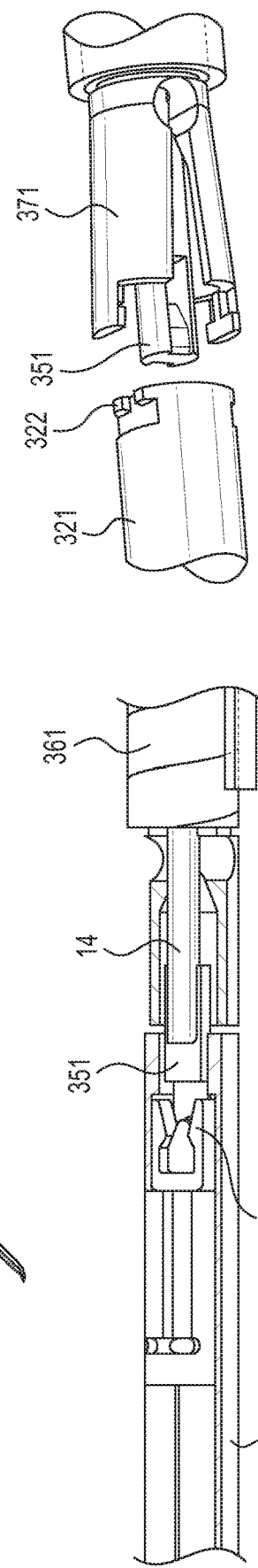

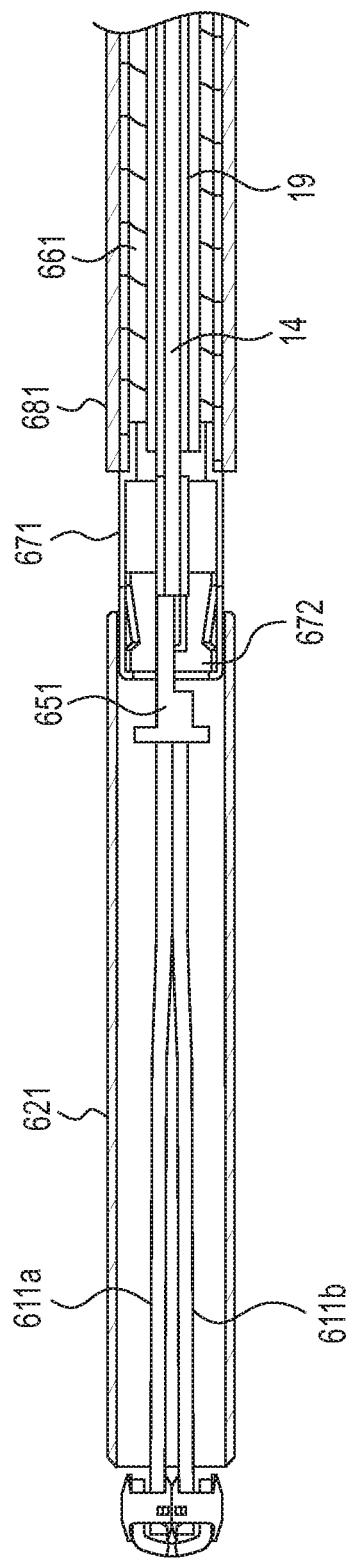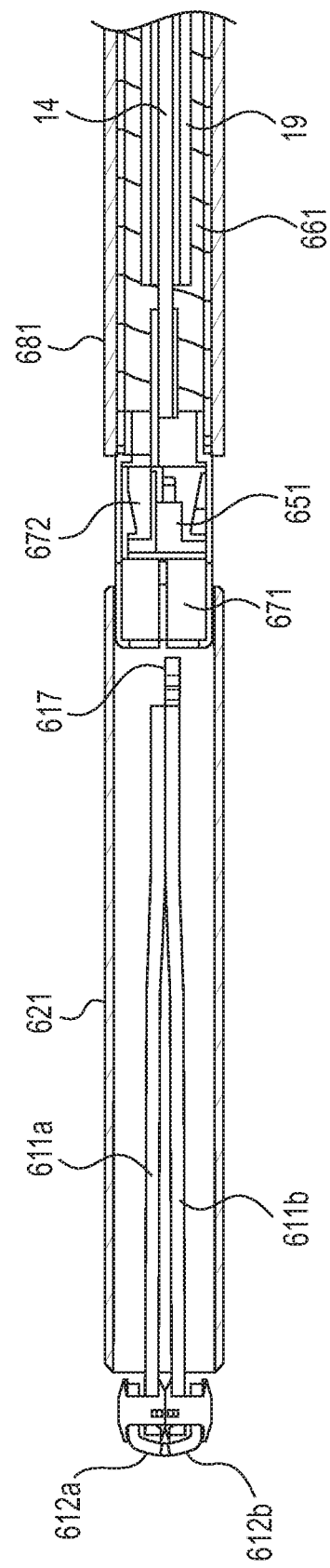

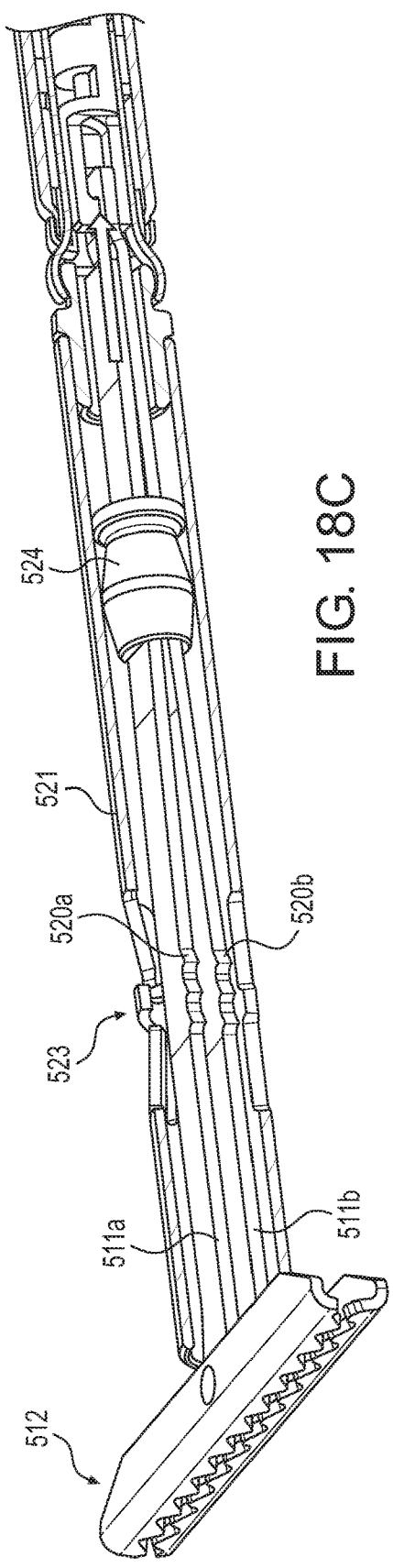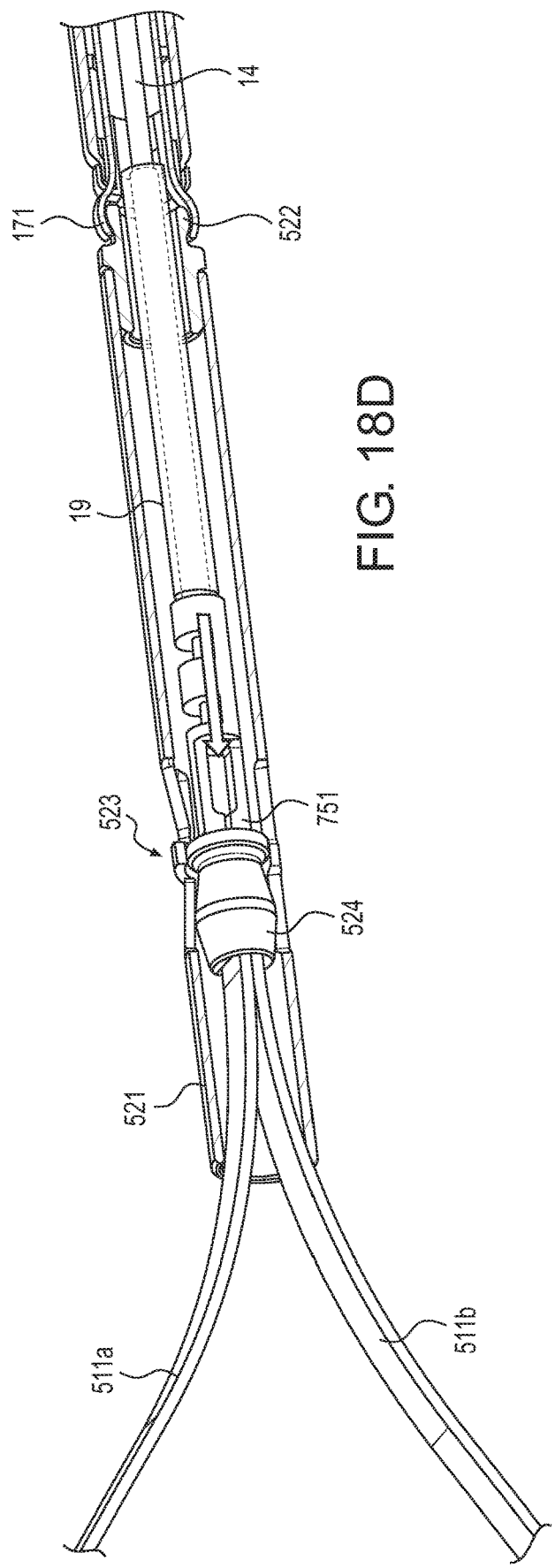

CLIPPING DEVICE FOR LARGE DEFECTS, PERFORATIONS AND FISTULAS

BACKGROUND

Closure devices can be used to treat wounds, incisions, defects, perforations, and fistulas and stop internal bleeding. Tissue or bodily walls can be perforated due to an injury, illness, or surgical procedure. For example, tissue or bodily walls may be injured, e.g., perforated, unintentionally during surgery, or may be perforated due to an illness or injury, such as a hernia. Sometimes tissue or bodily walls may be perforated intentionally, such as during surgical translumenal procedures. Perforations in luminal tissues, such as the gastrointestinal tract, must be controlled quickly to serious infections due to leakage of bodily fluids and other contents from the stomach or intestines into nearby bodily cavities.

A closure device can be introduced endoscopically to close the perforation and facilitate healing. For example, the closure devices may deliver a hemostasis clip to the target area within the body to clamp the tissue surrounding the perforation and stop bleeding or leakage of other bodily fluids and contents. Then, the closure device is removed, leaving the clips in place. The clips may be shed through natural processes or removed in a subsequent procedure after the wound has healed.

Depending on the size or shape of the perforation or the bodily structure that has been perforated, it can be difficult to adequately close the perforation and prevent leakage of bodily fluids. For example, hemostasis clips that are delivered through an endoscope, often referred to as "through-the-scope clip," cannot completely close large defects due to the limited opening width of the clip arm. Oftentimes many clips must be delivered to close the wound and stop bleeding and/or leakage of bodily fluids, which can make it difficult to completely close large perforations and can increase the possibility of complications.

Over-the-scope clips, on the other hand, are also problematic because it is necessary to retrieve the endoscope from the body to attach the closure device to the distal end of the endoscope before it can be deployed. Such over-the-scope closure devices are cumbersome to prepare and deploy. Additionally, retrieval of the endoscope during the procedure can cause the target area to loosen, and perforations can become bigger during preparation and attachment of the over-the-scope closure device to the endoscope. Delivery of over-the-scope clips often requires high skill. During deployment of the over-the-scope clips, suctioning is often used to pull the target tissue into the clip. But the suctioned target tissue often covers the lens of the endoscope, which can make it difficult or impossible to see the target area during clipping. The clip arm structure of over-the-scope clips can also make it difficult to deploy clips closely to one another in a side-by-side manner, and over-the-scope clips cannot be re-positioned after they have been deployed. Therefore, it can also be difficult to completely close large perforations with over-the-scope clips, especially if the clips are not deployed correctly, which can increase the possibility of complications A need thus exists for an improved device that can treat defects, perforations, and other wounds, including, large perforations, gastrointestinal perforations, fistulas, anastomotic leaks, and hernias, as well as other bodily defects and perforations in, for example, the esophagus, intestines, colon, stomach, and heart.

SUMMARY

The disclosed embodiments include a tissue clipping device and system, and method for clipping tissue.

The tissue clipping device includes a lock tube having a channel extending therethrough from a distal end to a proximal end, and a clip with clip arms that is at least partially disposed within a channel of the lock tube. The clip is designed to move distally and proximally relative to the lock tube between: an open configuration in which distal ends of the clip arms are separated from each other for receiving tissue therebetween, and a closed configuration in which the distal ends of the clip arms are closer to each other than in the open configuration for clipping the tissue received therebetween.

The tissue clipping system further includes a delivery device for delivering and deploying the tissue clipping device. The delivery device is releasably coupled to the tissue clipping device. The delivery device includes an insertion that is releasably coupled at a distal end to the proximal end of the lock tube, and a control member that extends through a channel of the insertion member and has a distal end that is releasably coupled to the proximal end of the clip.

The method for clipping tissue includes inserting a tissue clipping device into a body, advancing the clip distally out of a distal end of the lock tube so that the clip arms separate from each other in a radial direction to form an open configuration for receiving tissue; positioning the clip such that distal ends of the clip arms are adjacent to a portion of tissue surrounding a tissue opening to be closed; and advancing the lock tube distally relative to the clip such that the clip arms are contracted toward each other in a radial direction to form a closed configuration for clipping the tissue received between the clip arms.

Many modifications are possible without materially departing from the teachings of the detailed description. Accordingly, such modifications are intended to be included within the scope of the disclosure as defined in the claims.

BRIEF DESCRIPTION OF THE DRAWINGS

These and other aspects and features of the invention will become apparent to those of ordinary skill in the art upon review of the following description in conjunction with the accompanying figures.

FIG. 1A shows a tissue clipping device according to the disclosed embodiments.

FIGS. 1B and 1C show a delivery device according to the disclosed embodiments. FIG. 1B is a cross-sectional view of the delivery device shown in FIG. 1C.

FIGS. 6A-6C show a releasable lock tube connection mechanism according to the disclosed embodiments.

FIGS. 7A-7D show a releasable lock tube connection mechanism according to the disclosed embodiments.

FIGS. 12A-12F show a tissue clipping system according to the disclosed embodiments.

FIGS. 13A-13F show a tissue clipping system according to the disclosed embodiments.

FIGS. 14A-14G show a tissue clipping system according to the disclosed embodiments.

FIGS. 16A-16J show a tissue clipping system according to the disclosed embodiments.

FIGS. 18A-18E show a tissue clipping device locking mechanism according to the disclosed embodiments.

DETAILED DESCRIPTION OF EMBODIMENTS

Figure 2A:
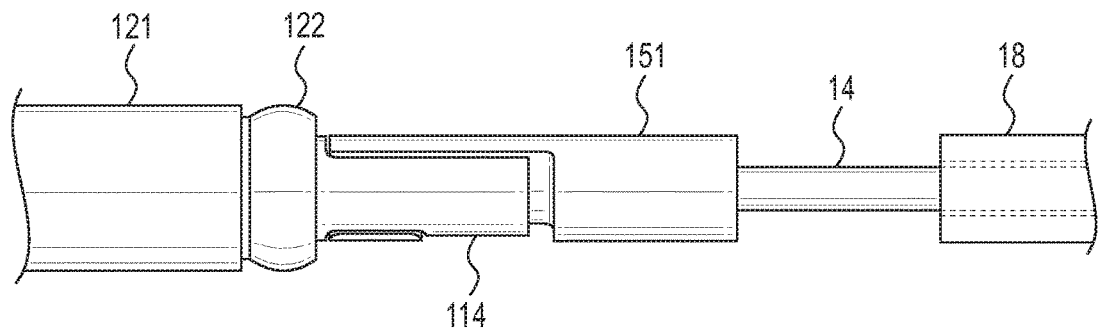
FIGS. 2A-2C show a releasable clip connection mechanism according to the disclosed embodiments.

The disclosed embodiments have been devised to address the above-mentioned problems. In particular, the disclosed embodiments include a tissue clipping device and system that can be delivered endoscopically to treat defects, perforations, and other wounds, including, for example, large defects and perforations, gastrointestinal perforations, fistulas, anastomotic leaks, and hernias, as well as other bodily defects and perforations in, for example, the esophagus, intestines, colon, stomach, and heart. The disclosed clipping device is able to close large defects, perforations, and fistulas quickly and accurately, with a reduced number of clips.

The device can be introduced without retrieving an endoscope already inserted in the patient, thereby eliminating the problems associated with having to retrieve an endoscope to prepare and attach the closure device to the endoscope. The device is capable of being deployed as close as possible to eliminate gap. For example, when multiple clips are used, the clips can be deployed closely in a side-by-side manner to eliminate gap. Additionally, the clipping device can be re-opened and re-adjusted before deploying. During deploying, the target area is visible through the endoscope. For example, suction may not be necessary to pull the tissue into the clip. As such, there is a reduced likelihood of tissue covering the lens of the endoscope. Therefore, the disclosed clipping device is capable of closing large defects, perforations, and fistulas with a reduced number of clips quickly and accurately, without specialized training. As a result, complications resulting from bleeding or leakage of bodily fluids, which may require re-intervention, can be reduced by use of the disclosed clipping device and system.

Various implementations are now described in detail in relation to the drawings. These exemplary implementations of the inventive principles are intended as illustrative only since numerous modifications and variations will be apparent to those skilled in the art.

The disclosed embodiments include a tissue clipping device and system, and a method for clipping tissue, as described below. FIG. 1A shows an exemplary clipping device 10 for gathering and clipping tissue to close defects, perforations, and fistulas. The clipping device 10 includes a clip 11 with clip arms for grasping and clipping tissue. The clip 11 is slidably disposed within a channel of a lock tube 12 so as to be moveable between an open configuration for receiving tissue there between and a closed configuration for clipping the tissue. The lock tube 12 is designed to compress the clip arms 11 radially inward so as to be in the closed configuration, and the clip arms of the clip 11 are designed to spring radially outward into the open configuration when the clip arms 11 are advanced out of a distal end of the lock tube 12. The clipping device 10 is releasably coupled to a delivery device for delivering and deploying the clipping device at the target area within the body. FIG. 1C shows an exemplary delivery device 13 for delivering the clipping device 10 to a target area in the body. FIG. 1B shows a cross-sectional view of the delivery device 13. For example, the delivery device 13 is designed to deliver the clipping device 10 to the target area, and advance the clip 11 out of a distal end 12a of the lock tube 12 such that the clip arms 11 spring radially outward into the open configuration for receive tissue therebetween. Then the lock tube 12 is advanced in the distal direction with respect to the clip 11 so as to draw the clip arms radially inward into the closed configuration for clipping the tissue received there between. When moving to the closed, tissue clipping configuration, the clip arms 11 are designed to draw the edges of the defect, perforation, or fistula together to close the perforation. Then, the clip 11 is designed to lockingly engage the lock tube 12 to lock the clip 11 in the closed, tissue clipping configuration to facilitate natural healing of the defect, perforation, or fistula. The clipping device 10 is then detached from the delivery device 13, and the delivery device 13 is retracted and removed from the body, with the clipping device 10 being left in place in the body.

As mentioned above, the clipping device 10 shown in FIG. 1A is designed to be detached or released from the delivery device 13 shown in FIGS. 1B and 1C and left in the body after the delivery 13 is removed. The clipping device 10 includes a clip 11 and a lock tube 12. The clip 11 is disposed within a channel of the lock tube 12 and includes a distal end 11a and a proximal end 11b. The distal end 11a of the clip 11 in FIG. 1A is shown protruding from a distal end 12a of the lock tube 12. For the purpose of illustration, the proximal end 11b of the clip 11 is shown extending out of the proximal end 12b of the lock tube in FIG. 1A. However, the proximal end 11b of the clip 11 may be housed within the channel of the lock tube 12 when the clip 11 is shown in the position of FIG. 1A. The proximal end 11b of the clip is designed to be releasably coupled to a clip connector 15 of the delivery device 13 for delivery and deployment of the clip 11 to the target area in the body.

The clip 11 includes clip arms that are coupled to each other at the proximal end 11b. In FIG. 1A, the clip 11 has radial arms, which are shown in a closed configuration. The clip arms may be radial clip arms 112 (shown in FIG. 12B) or radial clip arms 212 (shown in FIG. 13B), or the clip arms may have pivotable jaws 512 (FIG. 15A) or pivotable jaws 612 (FIG. 16B) coupled to a distal end 11a thereof. The radial arms 112, 212, and pivotable jaws 512, 612 are all designed to clip large perforations, defects, and fistulas. The specific features of the radial and jaw clip structures are discussed in more detail below.

The clip 11 is designed to move distally and proximally relative to the lock tube 12 between an open configuration and a closed configuration. In the open configuration, the distal ends 11a of the clip arms are separated from each other for receiving tissue therebetween (see FIGS. 12B, 12D, 13B, 14B, 14D, 16B). In the closed configuration, the distal ends 11a of the clip arms are closer to each other than in the open configuration for clipping tissue received therebetween and/or delivery of the clipping device, for example, through an endoscope (see FIGS. 12A, 12C, 13A, 13C, 13D, 13E, 14A, 14C, 15A, 15C, 16C, 16G, 16H, 16I, and 16D). The smaller profile of the closed configuration facilitates delivery of the clip 11 to the target area. The clip 11 may be made of an elastic material or shape memory material, such a nitinol, or any other suitable material so that the clip arms automatically radially expand when advanced distally out of a distal end 12a of the lock tube 12.

When the clipping device 10 is delivered to the target area, the clip 11 is advanced distally out of the distal end 12a of the lock tube 12 such that the clip arms are no longer constrained by the lock tube 12 such that the clip arms can radially expand to an open configuration for receiving tissue there between. For example, the clip arms 11 may be permitted to expand under a spring bias to the open, tissue-receiving configuration. Then, the lock tube 12 can be advanced in a distal direction with respect to the clip 11 so as to compress the clip arms towards one another and shift the clip 11 from the open configuration into the closed configuration to clip the tissue. After the clip 11 has been shifted to the closed configuration and tissue is clipped between the clip arms, the locking tube 12 may be advanced with respect to the clip such that the locking connector on the clip can engage a locking connector on the lock tube 12 to lock the clip 11 to the lock tube 12. Then, the clipping device 10 can be detached from the delivery device 13 so that the clipping device 10 can be left in the body while the delivery device 13 is retracted from the body.

The lock tube 12 is disposed around the clip 11 so as to house the clip 11 and restrain the clip arms from expanding into the open configuration when the clip arms are disposed inside the channel of the lock tube 12, as shown in FIG. 1A. The lock tube 12 is a substantially cylindrical hollow body having a channel extending there through that is sized so as to slidably receive the clip 11. The wall of the lock tube 12 is designed to radially compress the clip 11 to be in the closed configuration. The lock tube 12 may be slidable in proximal and distal directions with respect to the clip 11. As mentioned above, the lock tube 12 may include a locking connector for locking the clip 11 in the closed configuration after tissue has been clipped between the clip arms. Additionally, the proximal end 12b of the lock tube 12 is designed to be releasably coupled to a lock tube connector 17 comprised by the delivery 13 to facilitate delivery and deployment of the clipping device 10.

The lock tube 12 may include a flexible portion or may be flexible along its entire length such that the lock tube 12 can curve or bend to facilitate delivery through tortuous anatomy, as well as to facilitate deployment of the clipping device. For example, the lock tube 12 may bend to facilitate deployment of the clip 11 at the target area. The lock tube 12 or a portion, such as a distal portion thereof, may be processed by laser cutting so as to impart flexibility. For instance, the lock tube 12 may be made of stainless steel that has been laser processed to impart flexibility to a portion or entirety of the lock tube 12. As a result of laser processing, the lock tube 12 may have a cylindrical shape with gaps similar to a compressed spring. This structure improves flexibility of the lock tube 12 for accessing tortuous anatomy while also enabling excellent pushability and trackability through an endoscope.

The delivery device 13 shown in FIGS. 1B and 1C includes a control member 14 and an insertion member 16. The control member 14 is slidably disposed within a channel 165 of the insertion member 16. The control member 14 may be, for example, a control wire or guide wire, or may have any other suitable structure. The control member 14 includes a clip connector 15 designed to be releasably coupled to the proximal end 11b of the clip 11. The proximal end 11b of the clip 11 may be releasably coupled to the clip connector 15 via a hook connector, fork connector, or any other suitable releasable connection. Exemplary clip releasable connections are illustrated in FIGS. 2A-2C, 3A-3C, and 4, which are discussed in more detail below.

The insertion member 16 may be a spiral tube or any other flexible tube. For example, the insertion member 16 may be laser processed to impart flexibility, as discussed above with respect to the lock tube 12. A distal end of the insertion member 16 includes a lock tube connector 17 designed to be releasably coupled to the proximal end 12b of the lock tube 12. The proximal end 12b of the lock tube 12 may be releasably coupled to the lock tube connector 17 of the insertion member 16 via a ball and socket, frictional slider, wedge jaws, break-away, or bendable sheet connector, or any other suitable releasable connector. Exemplary lock tube release connections are shown in FIGS. 5A-5C, 6A-6C, 7A-D, 8A-8E, and 9A-9C, which are discussed in more detail below. The delivery device 13 also includes an inner liner 19 and an outer sheath 18. The inner liner 19 has a channel 195 through which the control member 14 slidably extends. The outer sheath 18 includes a channel 185 through which the insertion member 16 slidably extends.

The delivery device 13 is designed to deliver the clipping device 10 to the target area in the body. For example, the control member 14, which is releasably coupled to the clip 11, may be advanced or retracted to advance or retract the clip 11 with respect to the lock tube 12. Similarly, the insertion member 16, which is releasably coupled to the lock tube 12, may be advanced or retracted to advance or retract the lock tube 12 with respect to the clip 11. Once the clip 11 gathers and clips the tissue to close the perforation or defect and is locked in the closed configuration, the proximal end 11b of the clip 11 is released from the clip connector 15 of the control member 14, and the proximal end 12b of the lock tube 12 is released from the lock tube connector 17. The clip 11 may be released from the control member 14 before or after the lock tube 12 is released from the insertion member 16.

Exemplary tissue clipping systems are discussed below. All of the features discussed above with respect to clipping device 10 and delivery device 13 are equally applicable to the below discussed embodiment and thus are not repeated.

Figure 12A:
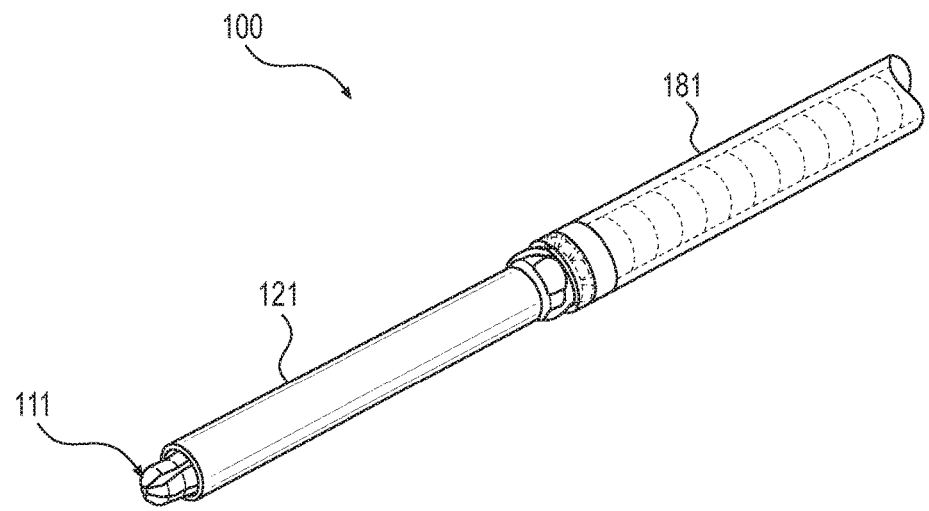
Figure 12B:
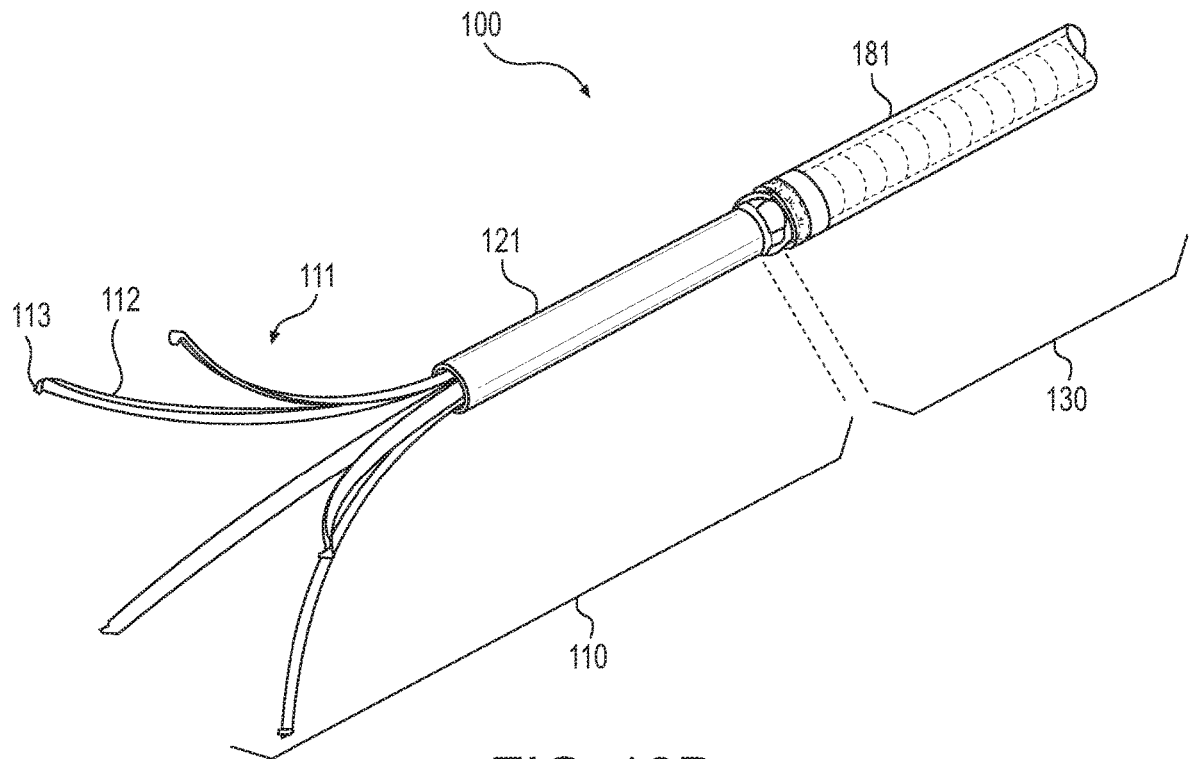

FIGS. 12A-12F show an exemplary clipping system 100 including a clipping device 110 that can be releasably coupled to a delivery device 130. As shown in FIGS. 12A and 12B, the clipping device 110 includes clip 111 and lock tube 121. The clipping device 110 is coupled to the delivery device 130 in FIG. 12A with the clip 111 in the closed configuration inside the channel of the lock tube 121 to facilitate delivery of the clipping device 110 to the target area in the body. The clipping device 110 may be described as being in the delivery configuration in FIG. 12A. In FIGS. 12B and 12D, the clipping device 110 is still coupled to the delivery device 130, but the clip 111 has been advanced distally out of the distal end of the lock tube 121 such that the clip arms 112 are in the open configuration. In other words, the clip 111 has been deployed to the target area and shifted to the open configuration to receive tissue between the clip arms 112.

The clip 111 includes radial arms 112 for grasping and clipping target tissue. FIG. 12B shows the clip 111 with five clip arms 112. However, the clip 111 may be designed with fewer or more clip arms 112 so long as the clip can securely clip tissue over a wide area. For example, the clip may have 3, 4, 5, or more clip arms to facilitate clipping over a wide area. The clip arms 112 may be spaced from each other by equal angles or may have any other suitable spacing. A radially outer side of each clip arm 112 is smooth and free of protrusions or detents, which could harm or damage the tissue. As shown in FIG. 12B, the clip arms 112 include a curvature radially outward to facilitate clipping larger defects, perforations, and fistulas. A distal, free end of each of the clip arms 112 includes a hook or barb 113 to facilitate grasping of the tissue by the clip arms 112. The clip arms 112 may alternatively include any other distal end suitable for facilitating grasping of the tissue, or the clip arms 112 may include blunt or rounded ends to reduce trauma to the tissue.

Figure 12C:
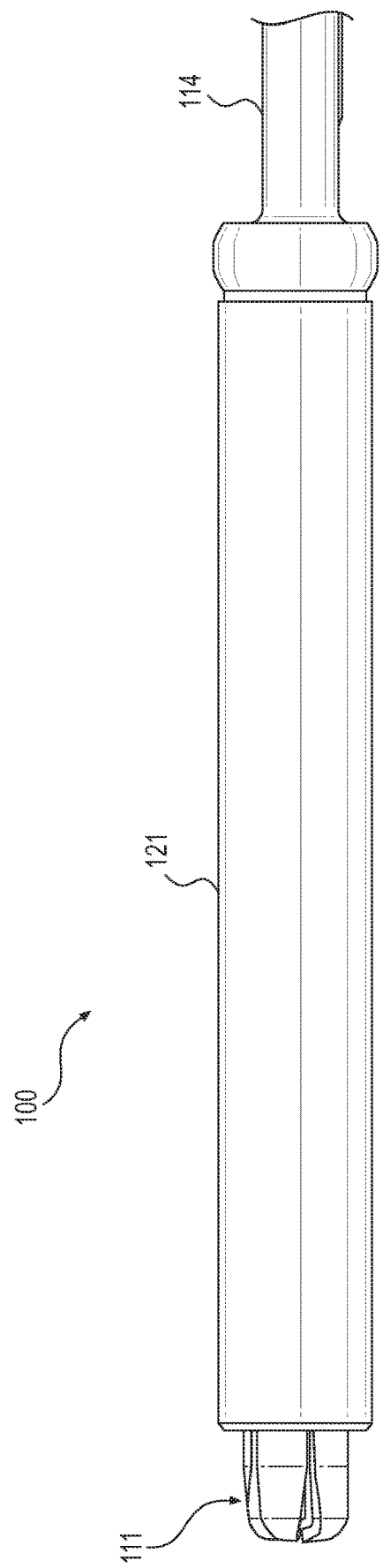

The clip 111 is slidably housed within a channel of the lock tube 121. The lock tube 121 is designed to radially compress the arms 112 of the clip 111 into the closed configuration as shown in FIGS. 12A and 12C. The arms 112 of the clip 111 are designed to radially expand into the open configuration when the clip 111 is advanced in the distal direction, as shown in FIGS. 12B and 12D. For example, the clip arms 112 may be under a spring bias so as to automatically expand into the open configuration when they are free of the lock tube 121.

Figure 12F:
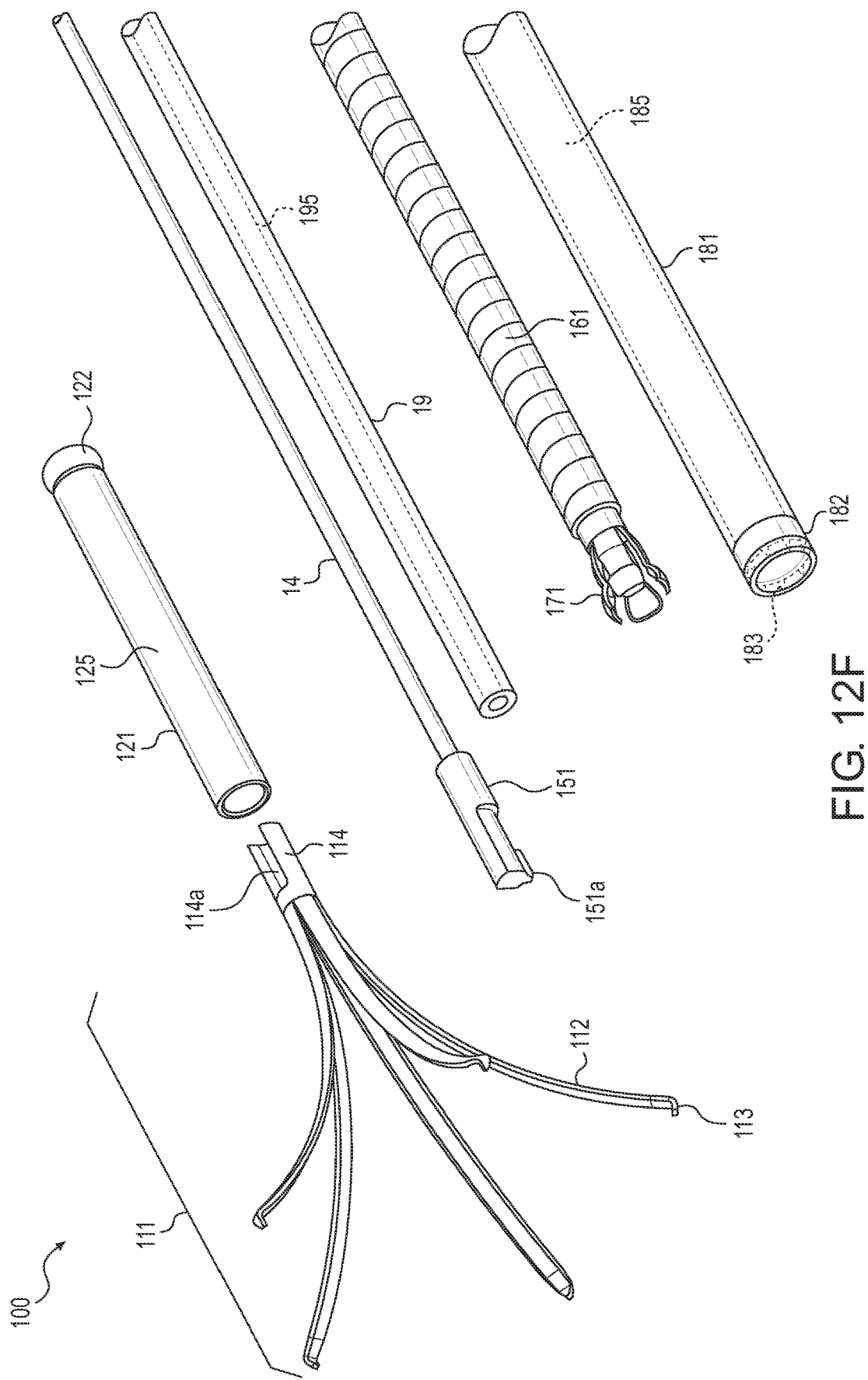

The delivery device 130 includes a control member 14, an inner liner 19, an insertion member 161, and an outer sheath 181 (see FIG. 12F). The outer sheath 181 is designed to surround an outer surface of the insertion member 161, but may not cover the clipping device 110 in this embodiment (see FIGS. 12A and 12B). As shown in the cross-sectional view of FIG. 12E, the control member 14 is received within a channel 195 of the inner liner 19, which is received within a channel 165 of the insertion member 161, which in turn is received within a channel 185 of the outer sheath 181.

The clipping device 110 is releasably coupled to the delivery device 130, as shown in FIGS. 12A, 12B, 12D, and 12E for delivery and deployment of the clipping device 110. In particular, as shown in FIG. 12E, a proximal end 114 of the clip 111 is coupled to a hook connector 151 on the distal end of the control member 14, and a proximal end 122 of the lock tube 121 is coupled to a socket connector 171 on the distal end of the insertion member 161.

Figure 2B:
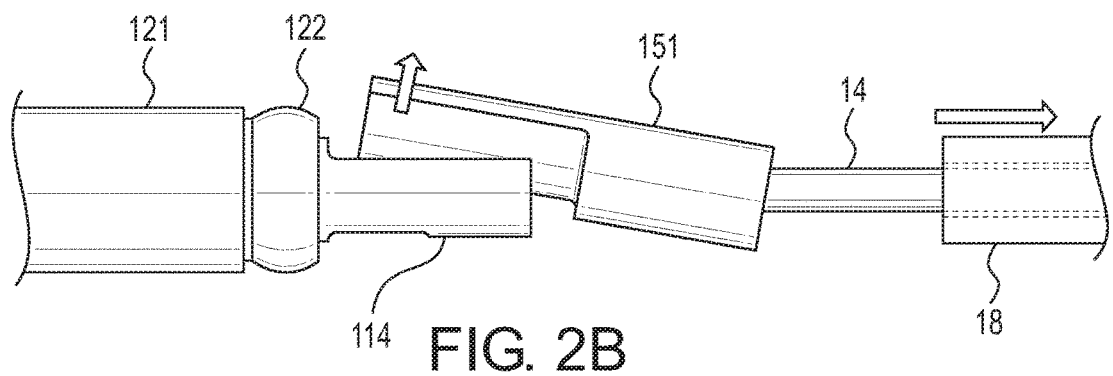
Figure 2C:
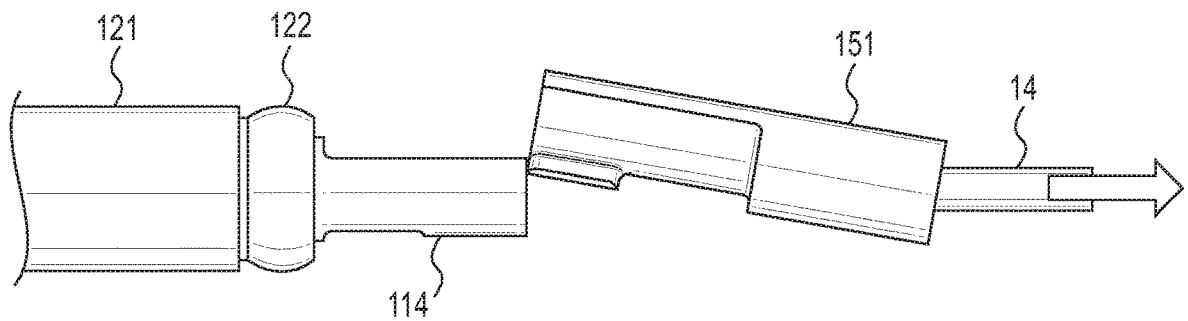

Detailed views of the hook connection mechanism between the clip 111 and the control member 14 are shown in FIGS. 2A-2C. The hook connector 151 is releasably coupled to a proximal end 114 of the clip 111 in FIG. 2A. For example, the hook connector 151 may include a hook 151a that can releasably engage an opening 114a in the proximal end 114 of the clip (see FIG. 12F). The hook connector 151 is designed to release the clip 111 after the lock tube 121 is released from the lock tube connector 17 by retracting the control member 14. Once the hook connector 151 is exposed from the proximal end of the lock tube 121, retraction of the control member 14 causes the hook connector 151 to pivot with respect to the control member 14 to disengage the proximal end 114 of the clip 111. That is, the hook connector 151 is no longer confined by the lock tube 121 or insertion member 161. Therefore, the hook connector 151 can pivot to disengage the proximal end 114 of the clip 111. Then, retraction of the control member 14 continues in FIG. 2C to remove the delivery device 13 from the body.

Figure 5A:
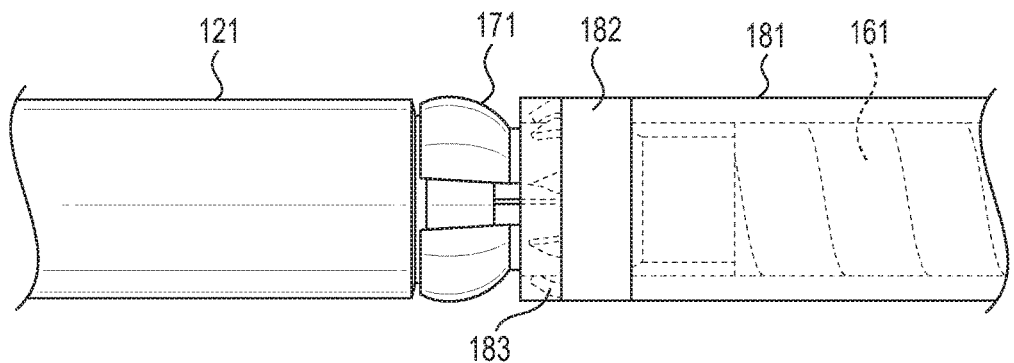
FIGS. 5A-5C show a releasable lock tube connection mechanism according to the disclosed embodiments.
Figure 5B:
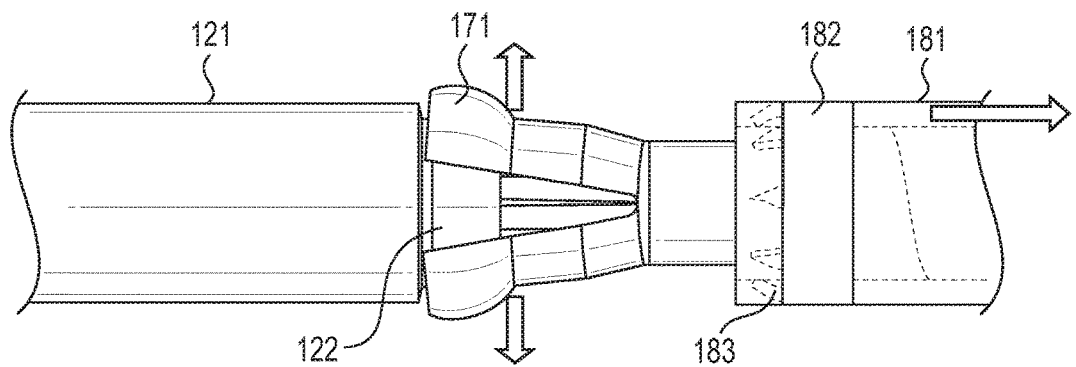
Figure 5C:
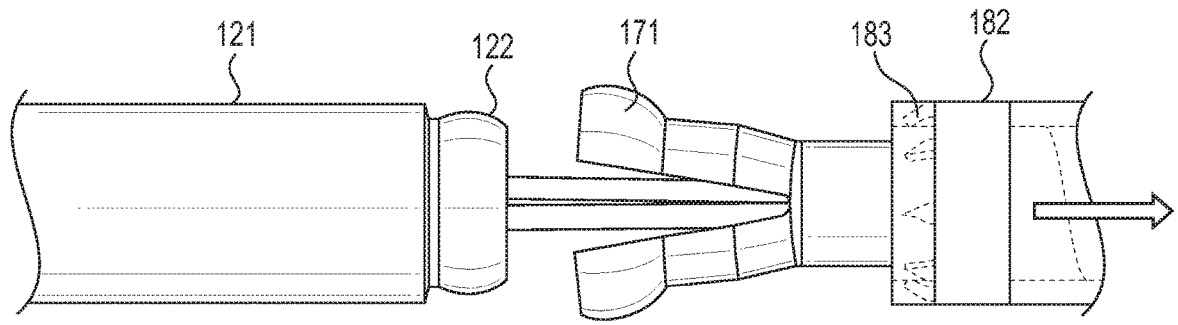

Detailed view of the ball-and-socket connection mechanism between the lock tube 121 and the insertion member 161 are shown in FIGS. 5A-5C. The socket connector 171 on the distal end of the insertion member 161 is designed to hold the ball connector 122 formed on the proximal end of the lock tube 121 by virtue of lock ring 182 formed on the outer sheath 181. The socket 171, which is spring loaded outward, can be compressed by the lock ring 182 including lock teeth 183 to hold the ball 122 on the proximal end of the lock tube 121. As shown in FIG. 5A, the lock tube 121 is releasably coupled to the socket connector 171 of the insertion member 161 by virtue of the lock ring 182 including the lock teeth 183 being positioned around the proximal portion of the socket 171 to compress the socket 171 around the ball 122 on the proximal end of the lock tube 121. The socket connector 171 is designed to release the lock tube 121 by retracting the outer sheath 181 with respect to the insertion member 161, as shown in FIG. 5B. Once the outer sheath 181 has been retracted such that the lock ring 182 releases the socket 171, the socket 171 automatically springs open (e.g., the socket arms 171 separate in a radial direction) to release the ball connector 122 formed on the proximal end of the lock tube 121, as shown in FIG. 5C. Although the exemplary embodiment shown in FIGS. 12A-F employs the ball-and-socket connection with the hook connector 151, the lock tube ball-and-socket connection structure is compatible with any of the hook 151, hook 551, fork 312, fork 617, or alternative fork 751 connectors, which are discussed below. In the exemplary embodiment shown in FIGS. 12A-12E, the ball-and-socket connection between the lock tube 121 and the insertion member 161 is somewhat flexible.

Figure 13A:
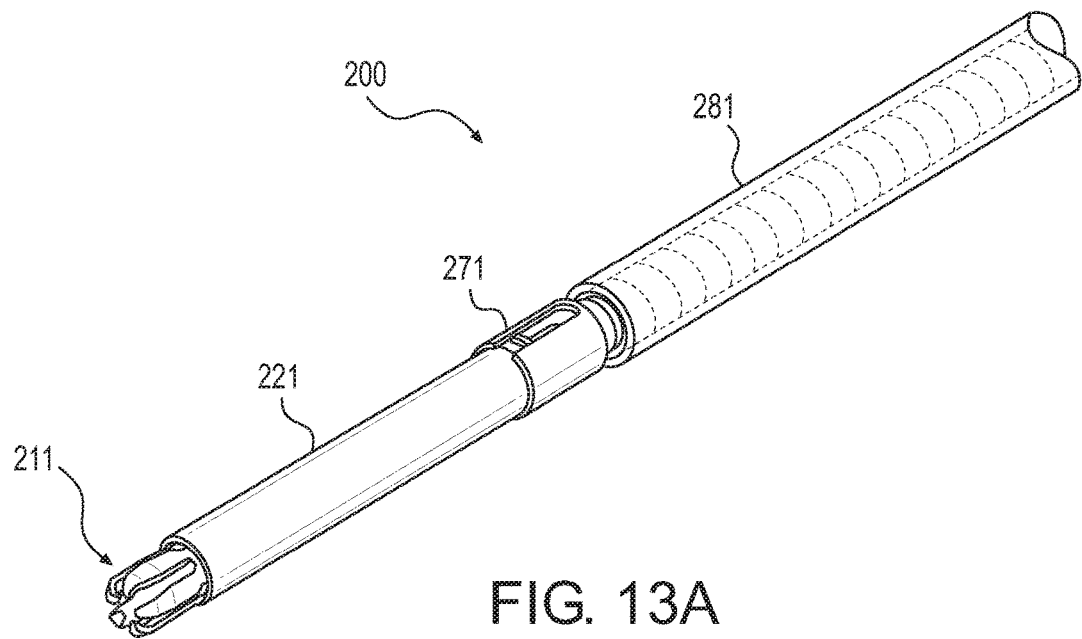
Figure 13B:
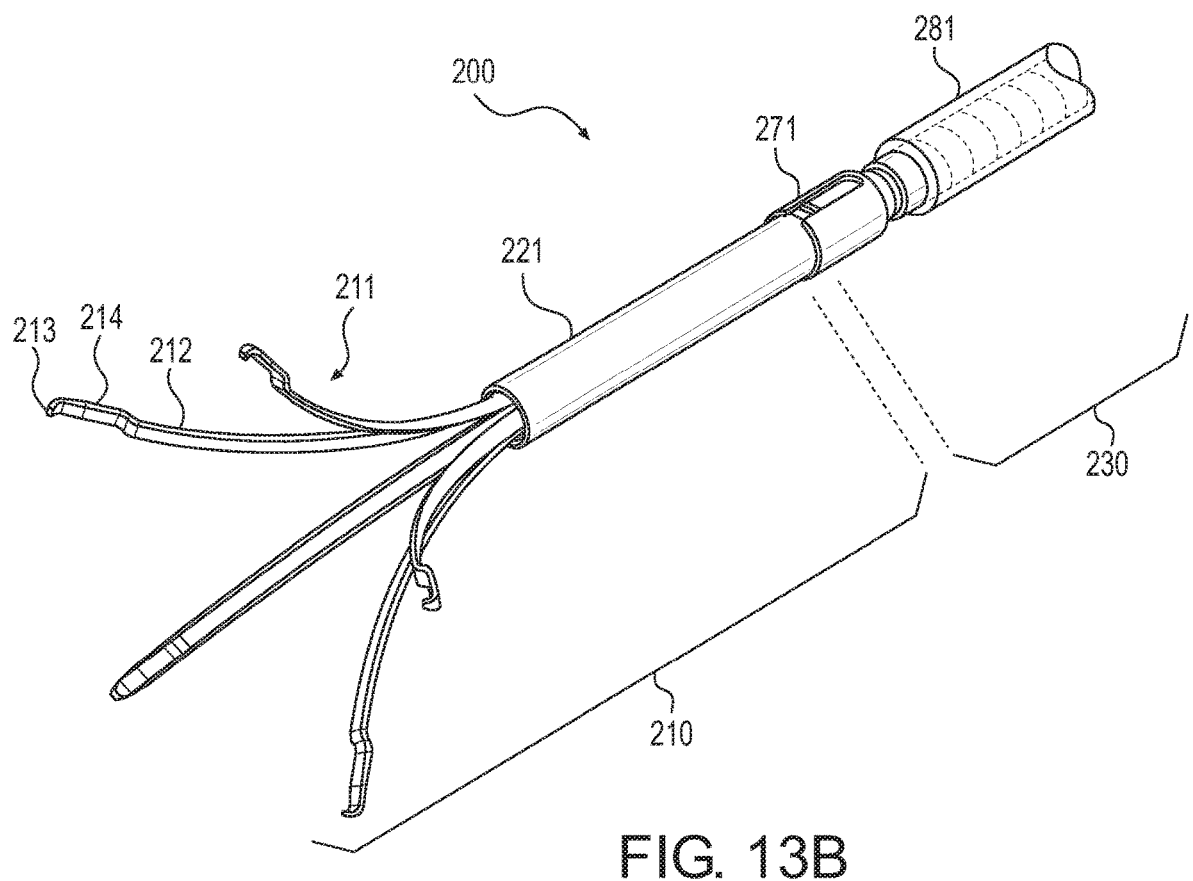

FIGS. 13A-13F show an exemplary tissue clipping system 200 including a clipping device 210 and a delivery device 230 that are releasably coupled to one another. As shown in FIGS. 13A and 13B, the clipping device 210 includes clip 211 and lock tube 221. The clipping device 210 is coupled to the delivery device 230 in FIG. 12A with the clip 211 in the closed configuration inside the channel of the lock tube 221 to facilitate delivery of the clipping device 210 to the target area in the body. The clipping device 210 may be described as being in the delivery configuration in FIG. 13A. In FIG. 13B, the clipping device 210 is still coupled to the delivery device 230, but the clip 211 has been advanced distally out of the distal end of the lock tube 221 such that the clip arms 212 are in the open configuration. In other words, the clip 211 has been deployed to the target area and shifted to the open configuration to receive tissue between the clip arms 212.

The clip 211 includes radial clip arms 212 for grasping and clipping target tissue. Radial clip arms 212 are the same as clip arms 112 in the embodiment discussed above with respect to FIGS. 12A-12F except that clip arms 212 further include an abutment arch 214 on the distal end. The arch 214 serves as an abutment against which the lock tube 221 is designed to abut for facilitating detachment of the lock tube 221 from the delivery device 230, as discussed in more detail below.

Figure 13C:
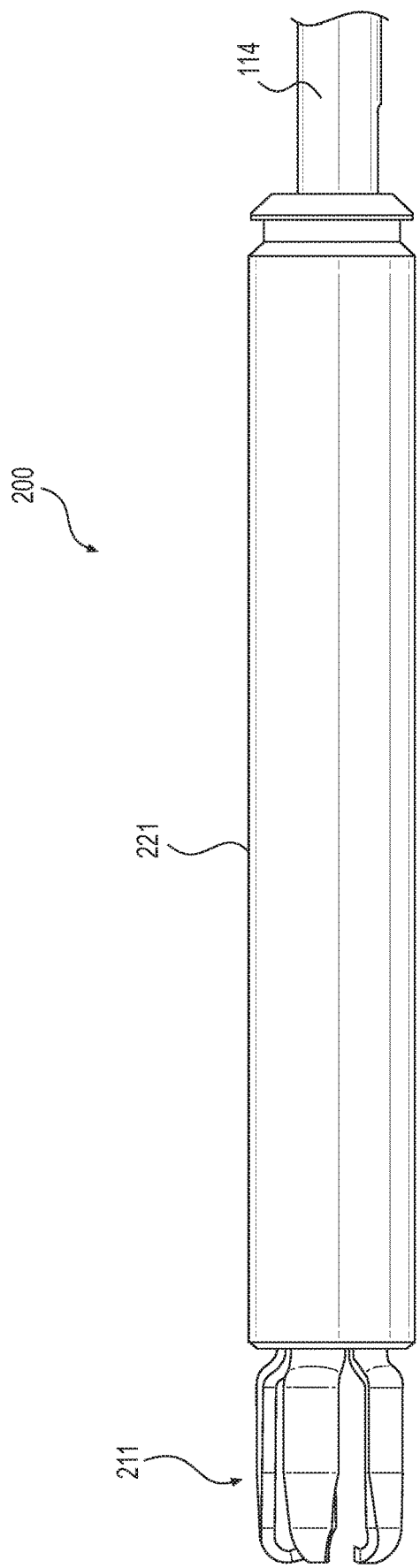

The clip 211 is slidably housed within a channel of the lock tube 221. The lock tube 221 is designed to radially compress the arms 212 of the clip 211 into the closed configuration as shown in FIGS. 13A, 13C, and 13D. The arms 212 of the clip 211 are designed to radially expand into the open configuration when the clip 211 is advanced in the distal direction, as shown in FIG. 13B. For example, the clip arms 212 may be under a spring bias so as to automatically expand into the open configuration when they are free of the lock tube 221. The lock tube 221 in the present embodiment is capable of rotating with the clip arms 212.

Figure 13F:
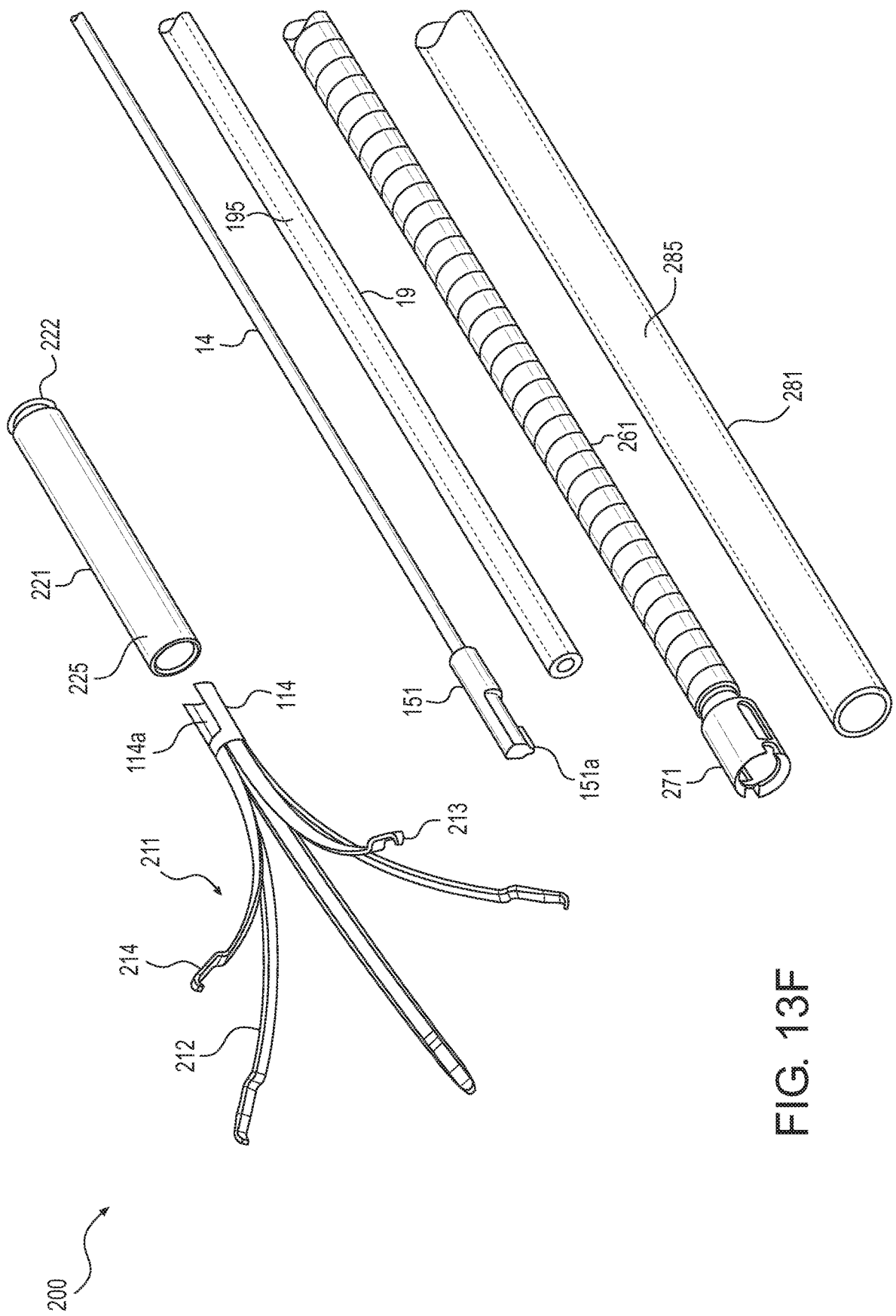

The delivery device 230 includes a control member 14, an inner liner 19, an insertion member 261, and an outer sheath 281 (see FIG. 13F). The outer sheath 281 is designed to surround an outer surface of the insertion member 261, but may not cover the clipping device 210 (see FIGS. 13A and 13B). The control member 14 is received within a channel 195 of the inner liner 19, which is received within a channel 265 of the insertion member 261, which in turn is received within a channel 285 of the outer sheath 281.

The clipping device 210 is releasably coupled to the delivery device 230, as shown in FIGS. 13A, 13B, 13D, and 13E for delivery and deployment of the clipping device 210. In particular, as shown in FIGS. 13D and 13E, a proximal end 114 of the clip 211 is coupled to a hook connector 151 on the distal end of the control member 14, and a proximal end 222 of the lock tube 221 is coupled to a break-away connector 271 on the distal end of the insertion member 261.

The hook connection between the hook connector 151 and the proximal end 114 of clip 211 is the same as that discussed above, and thus, is not repeated here.

Figure 8A:
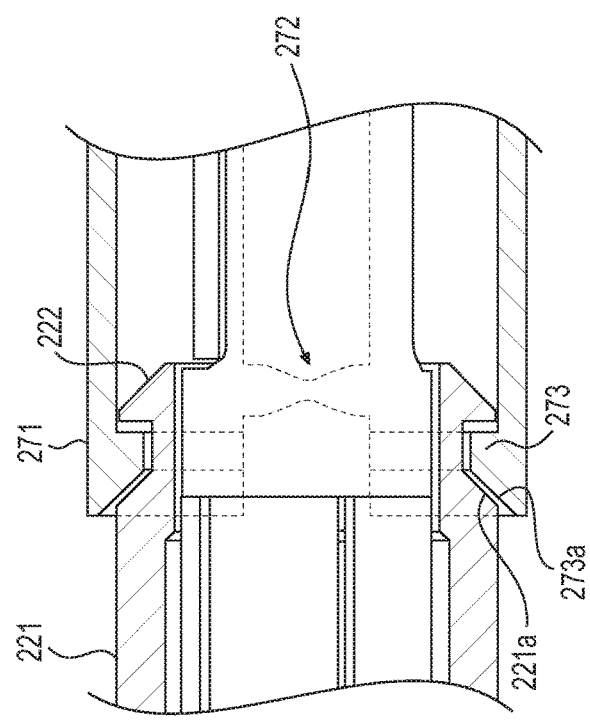
FIGS. 8A-8E show a releasable lock tube connection mechanism according to the disclosed embodiments.
Figure 8B:
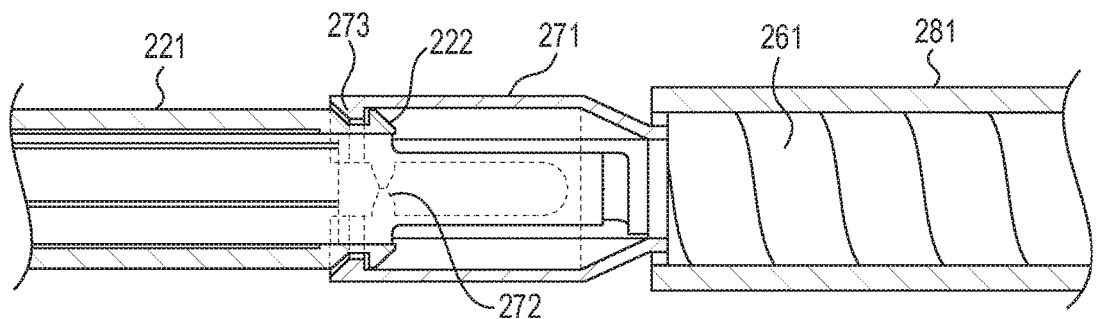
Figure 8C:
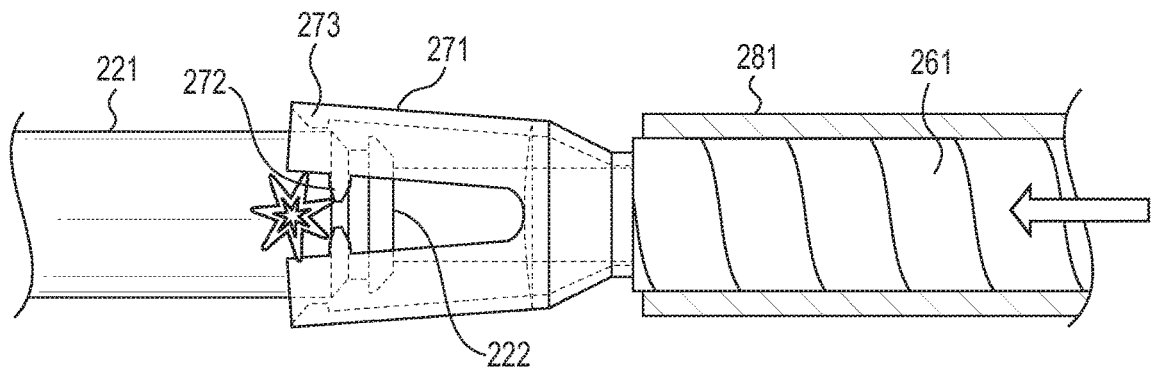
Figure 8D:
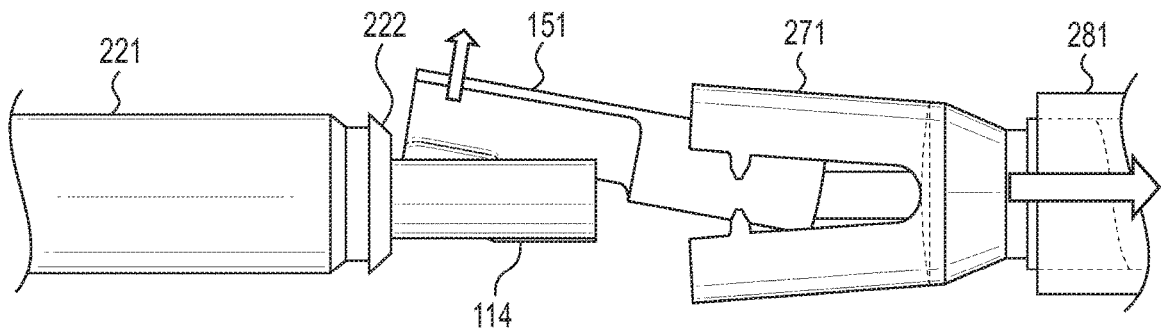
Figure 8E:
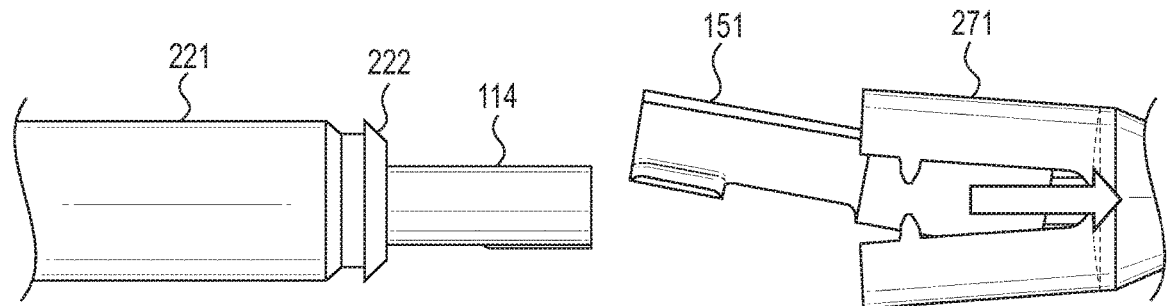

Detailed views of the break-away connector 271 for releasably coupling the lock tube 221 to the insertion member 261 are shown in FIGS. 8A-8E. A lip 273 formed on an inner surface of the break-away connector 271 is designed to engage a connector lip 222 formed on an outer surface of the proximal end of the lock tube 221, as shown in FIGS. 8A and 8B. The break-away connector 271 includes a break-away portion 272, which is intact in FIGS. 8A and 8B (see also FIG. 13E). To disengage the lock tube 221 from the break-away connector 271, the insertion member 261 is advanced distally a short distance in the distal direction with respect to the lock tube 221. When the insertion member 261 is advanced in the distal direction, the distal end of the lock tube 221 abuts against the arched abutment 241 formed on the distal end of the clip arms 212, as shown in FIG. 13D. As such, the lock tube 221 is prevented from advancing with the insertion member 261. That is, the insertion member 261 is able to advance a short distance in the distal direction with respect to the lock tube 221 in order to break the break-away portion 272. When the insertion member is advanced in the distal direction, a tapered surface 273a of lip 273 is advanced along tapered surface 221a of the lock tube 221 (see FIG. 8A) such that a radially outward force is exerted on the walls of the break-away connector 271, and a breaking force is exerted on the break-away portion 272. As a result, the break-away portion 272 breaks, as shown in FIG. 8C. Then, the insertion member 261 is retracted proximally to fully separate the break-away connector 271 from the proximal end 222 of the lock tube 221. After disengaging the break-away connector 271 and the proximal end 222 of the lock tube 221, the hook connector 151 can be released from the proximal end 114 of the clip 111, as shown in FIGS. 8D and 8E, and as discussed above.

In the exemplary embodiments shown in FIGS. 12A-12F and 13A-13F, the sheaths 181, 281 are not designed to cover the clips 111 and 211. However, the clipping system is not limited to such a configuration. For example, in the exemplary embodiment discussed below, the sheath 381 is designed to cover the clip 311.

Figure 14A:
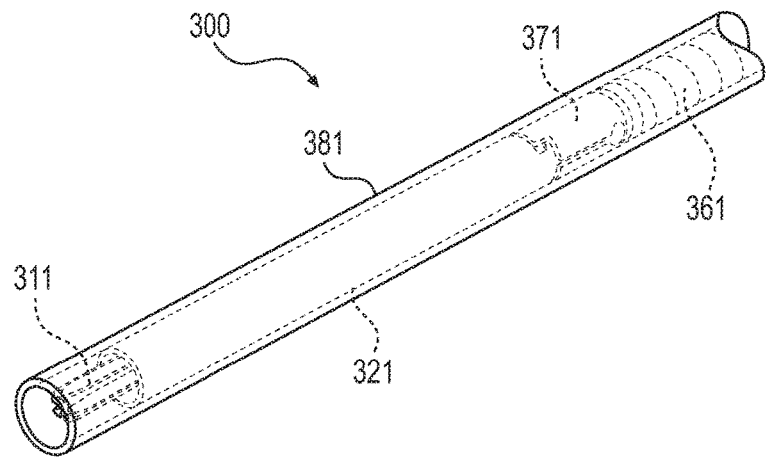
Figure 14B:
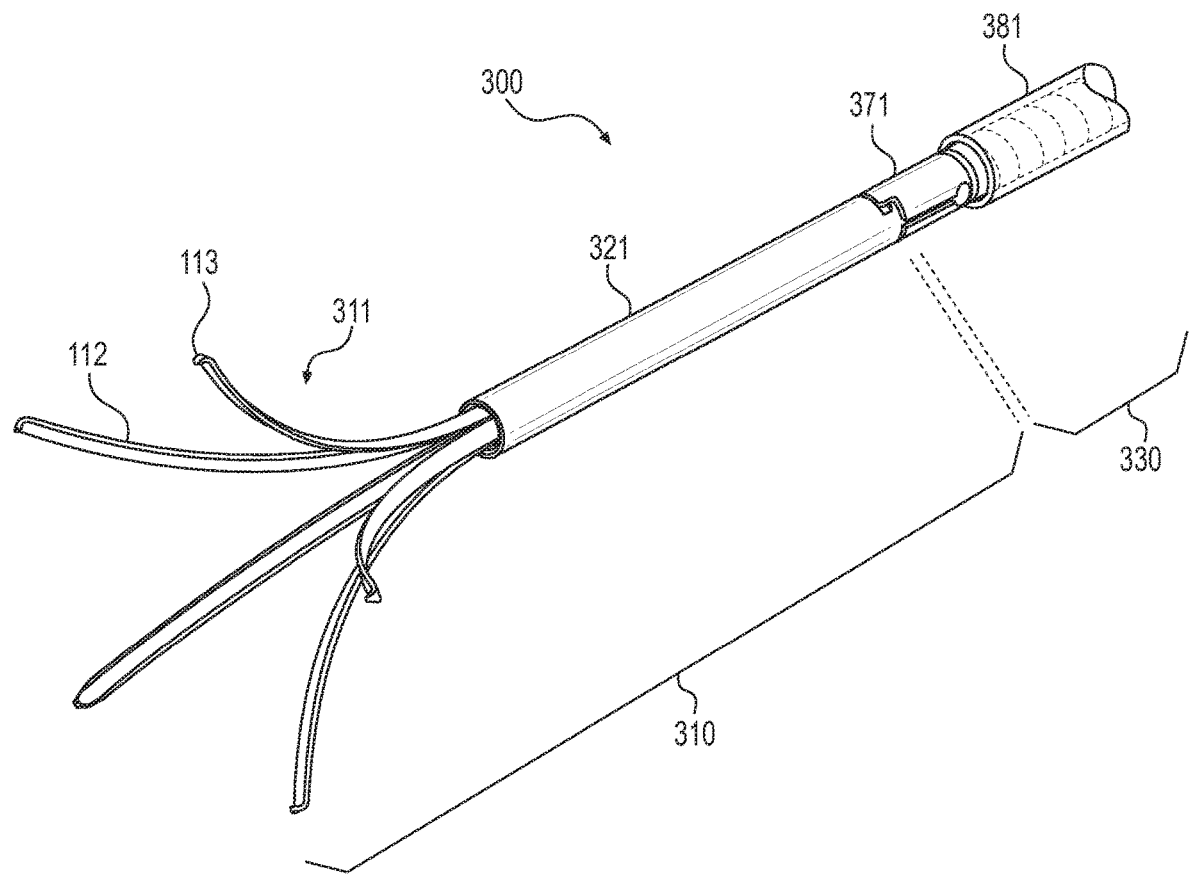

FIGS. 14A-14G show an exemplary tissue clipping system 300 including a clipping device 310 releasably coupled to a delivery device 330. As shown in FIG. 14A, the clipping device 310 includes clip 311 and lock tube 321. The clipping device 310 is coupled to the delivery device 330 in FIG. 14A with the clip 311 in the closed configuration inside the channel of the lock tube 321 to facilitate delivery of the clipping device 310 to the target area in the body. The sheath 381 of the delivery device 330 is designed to cover the clipping device 310, as shown in FIG. 14A. The clipping device 310 may be described as being in the delivery configuration in FIG. 14A. In FIGS. 14B and 14D, the clipping device 310 is still coupled to the delivery device 330, but the sheath 381 has been retracted proximally and/or the clipping device 310 has been advanced distally out of the sheath 381, and the clip 311 has been advanced distally out of the distal end of the lock tube 321 such that the clip arms 112 are in the open configuration. In other words, the clip 311 has been deployed to the target area and shifted to the open configuration to receive tissue between the clip arms 112.

The clip 311 includes radial arms 112 for grasping and clipping target tissue. Radial clip arms 112 are the same as clip arms 112 in the embodiment discussed above with respect to FIGS. 12A-12F.

The clip 311 is slidably housed within a channel of the lock tube 321. The lock tube 321 is designed to radially compress the arms 112 of the clip 311 into the closed configuration as shown in FIGS. 14A and 14C. The arms 112 of the clip 311 are designed to radially expand into the open configuration when the clip 311 is advanced in the distal direction, as shown in FIGS. 14B and 14D. For example, the clip arms 112 may be under a spring bias so as to automatically expand into the open configuration when they are free of the lock tube 321.

The delivery device 330 includes a control member 14, an inner liner 19, an insertion member 361, and an outer sheath 381 (see FIG. 12F). The outer sheath 381 is designed to surround an outer surface of the insertion member 361, and may cover the clipping device 310, for example, during delivery of the clipping device 310 to the target area in the body (see FIG. 14A). As shown in the cross-sectional view of FIGS. 14D and 14E, the control member 14 is received within a channel 195 of the inner liner 19, which is received within a channel 365 of the insertion member 361, which in turn is received within a channel 385 of the outer sheath 381.

The clipping device 310 is releasably coupled to the delivery device 330, as shown in FIGS. 14A, 14B, 14D, and 14E for delivery and deployment of the clipping device 310. In particular, as shown in FIGS. 14D and 14E, a fork connector 312 is formed on the proximal end of the clip 311, which is releasably coupled to a clip connector 351 on the distal end of the control member 14. A proximal end 322 of the lock tube 321 is coupled to a wedge jaws connector 371 on the distal end of the insertion member 361.

Figure 3A:
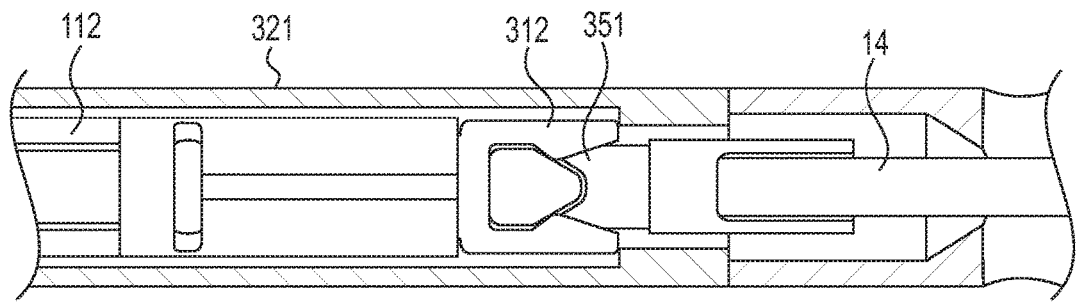
FIGS. 3A-3C show a releasable clip connection mechanism according to the disclosed embodiments.
Figure 3B:
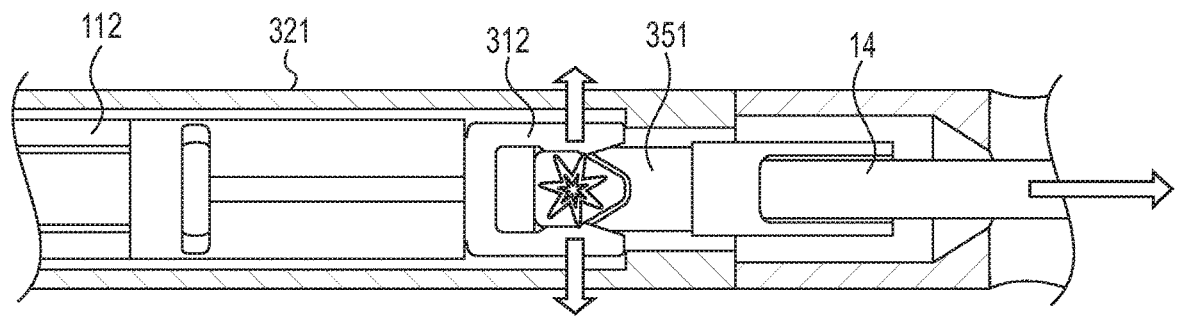
Figure 3C:
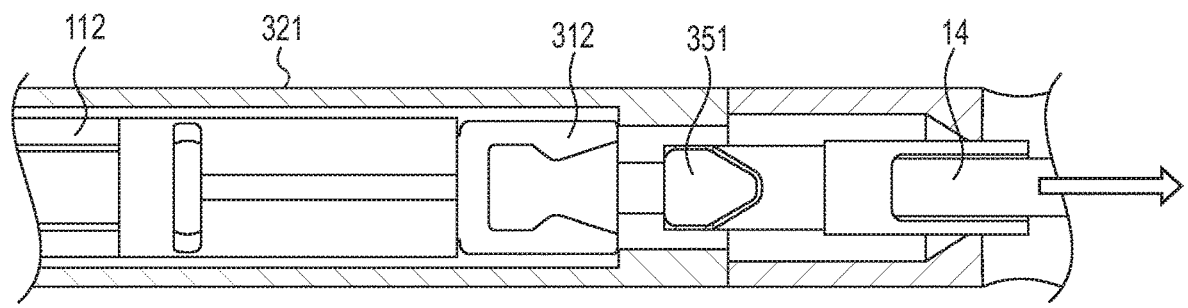
Figure 14G:
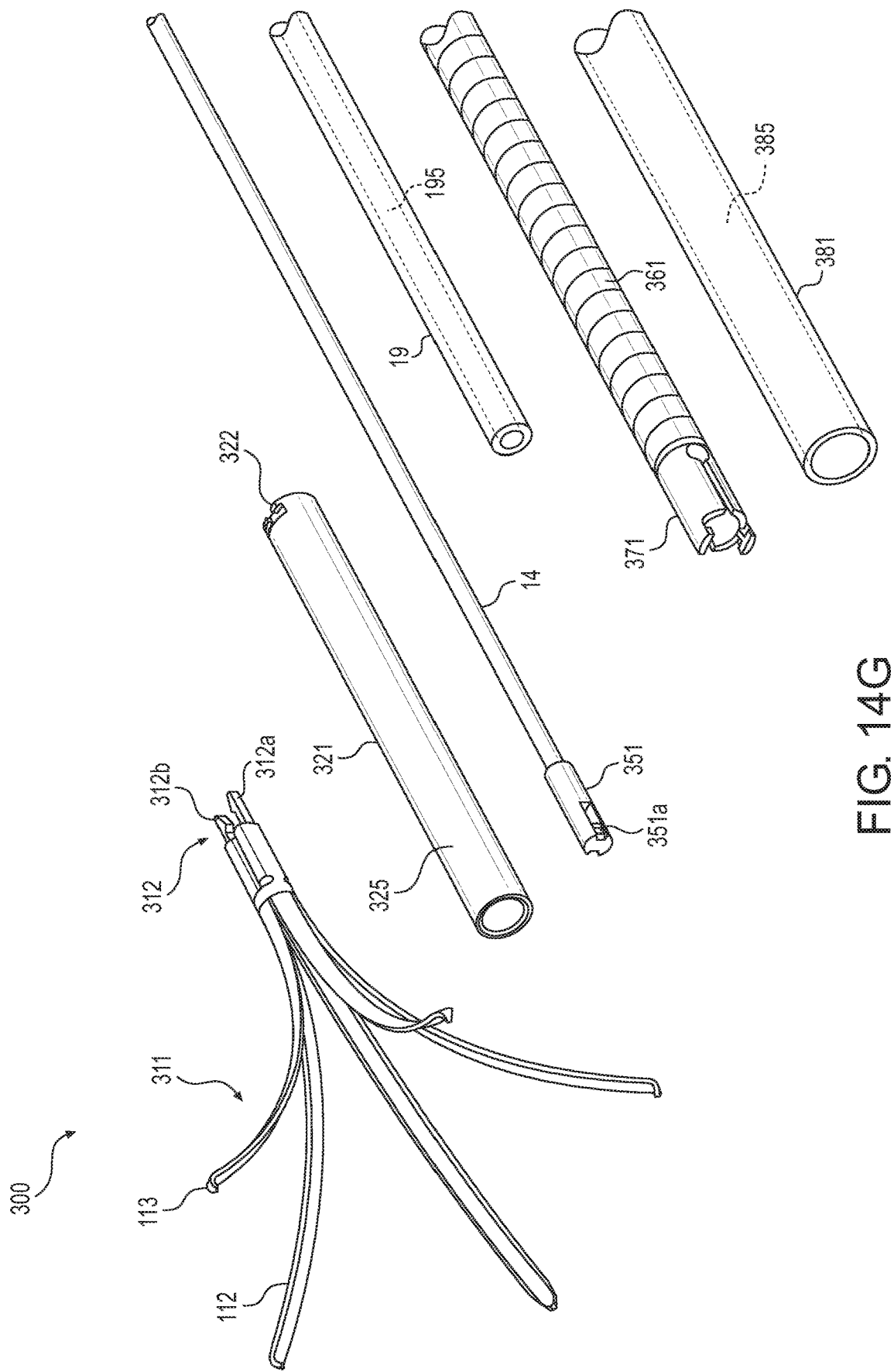

Detailed view of the fork connector mechanism between the fork connector 312 at the proximal end of the clip 3111 and the clip connector 351 formed on a distal end of the control member 14 are shown in FIGS. 3A-3C. As shown in FIG. 14G, the connector 351 may include a catch 351a having a smaller diameter than a remainder of the connector 351. The catch 351a can be received within the area defined by fork arms 312a, 312b of the fork connector 312 of the clip 311 to detachably couple the clip 311 and the control member 14 of the delivery device 13. For instance, the fork connector 312 of the clip 311 is releasably coupled to the clip connector 351 of the control member 14 in FIG. 3A. The fork connection is released by retracting the control member 14 after the clip 311 has been locked to the lock tube 321 in the closed position, but before the lock tube 321 has been disengaged from the lock tube connector 371. Retraction of the control member 14 causes the arms of the fork connector 312 to spread in a radial direction to release the catch 351a of the clip connector 351, as shown in FIG. 3B. That is, the fork connector arms 312 radially separate in response to the pulling force of the catch 351a there through. As shown in FIG. 14G, the catch 351a may have tapered surfaces to facilitate disengagement of the catch 351a from the fork arms 312a, 312b. Similarly, the fork arms 312a and 312b may also be tapered. The clip connector 351 is then completely disengaged from the fork connector 312, as shown in FIG. 3C.

Figure 7A:
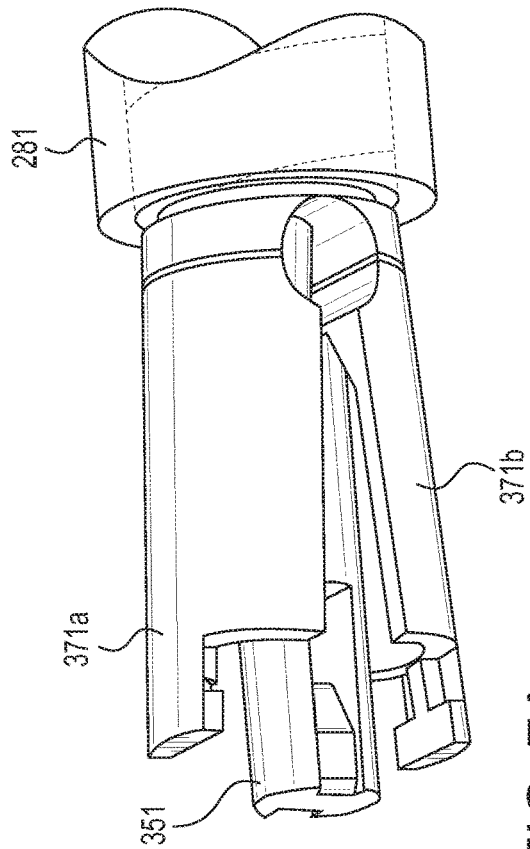
Figure 7A:
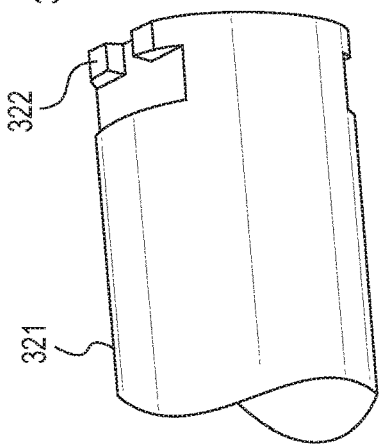
Figure 7D:
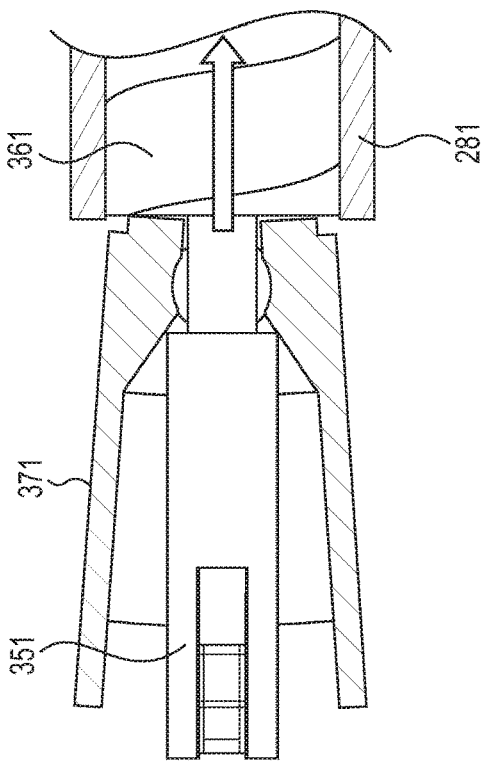

Detailed view of the wedge arms connection mechanism between the wedge jaws connector 371 on the distal end of the insertion member 361 and the proximal end of the lock tube 321 are shown in FIGS. 7A-7D. As shown in FIG. 7A, the wedge arm connector 371 includes jaws 371a, 371b that releasably engage connector 322 on the proximal end of the lock tube 321. The lock tube 321 is coupled with the wedge arm connector 371 in FIG. 7B. The wedge jaws connector 371 is designed to release the lock tube 321 by pulling the control member 14 in the proximal direction. This causes the fork connector 312 on the proximal end of the clip 311 to disengage clip connector 351 on the distal end of the insertion member 361, as shown in FIG. 7B. Continued retraction of the control member 14 forces the wedge jaws connector 371 to open and release the proximal end connector 322 of the lock tube 321, as shown in FIG. 7C. In particular, the wedge jaws 371a, 371b are separate from one another in the radial direction to release connector 322 on the proximal end of the lock tube 321. Then, the locking tube 321 can be fully released from the wedge jaws connector 371 as shown in FIG. 7D such that the locking device 10 is fully released from the delivery device 13. The wedge jaws connector 371 is compatible with the fork connector 312 (which is the same as 617), as well as the alternative fork connector 751.

In the exemplary embodiments discussed above, the clips 111, 211, and 311 included radial clip arms 112, 212 for gather and clipping tissue. However, the clipping device is not limited to such a configuration. For example, the clip may alternatively include pivotable jaws on a distal end of the clip arms for gathering and clipping the tissue, as discussed in the below exemplary embodiment.

Figure 15A:
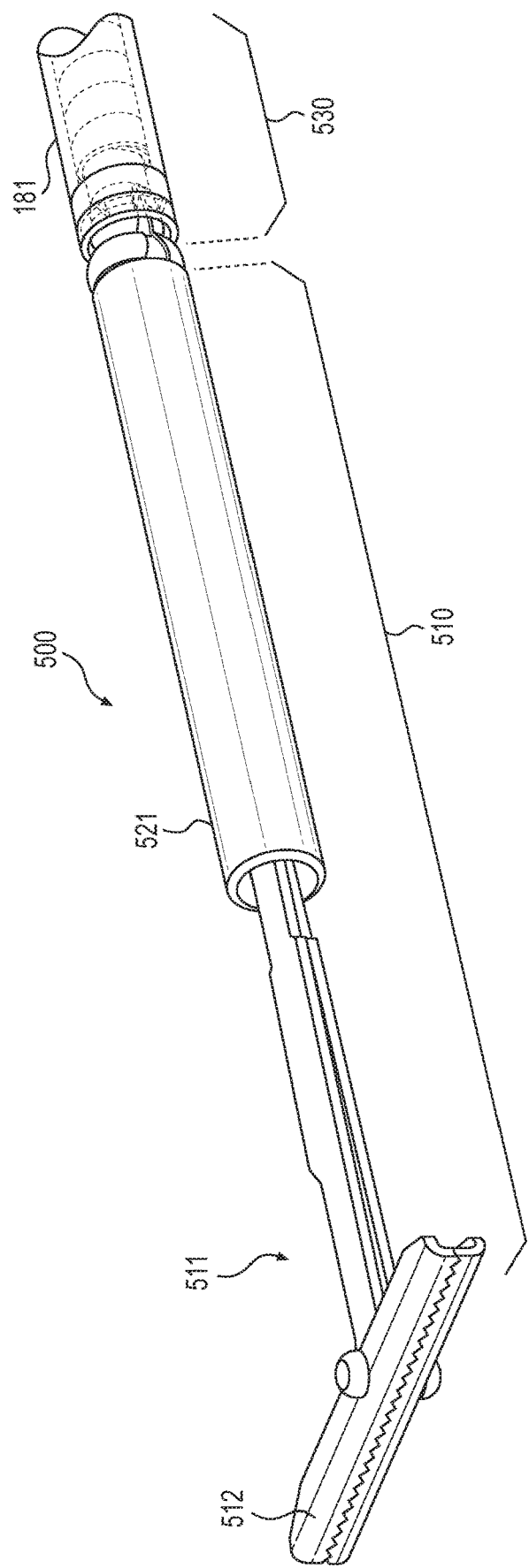
FIGS. 15A-15D show a tissue clipping system according to the disclosed embodiments.
Figure 15B:
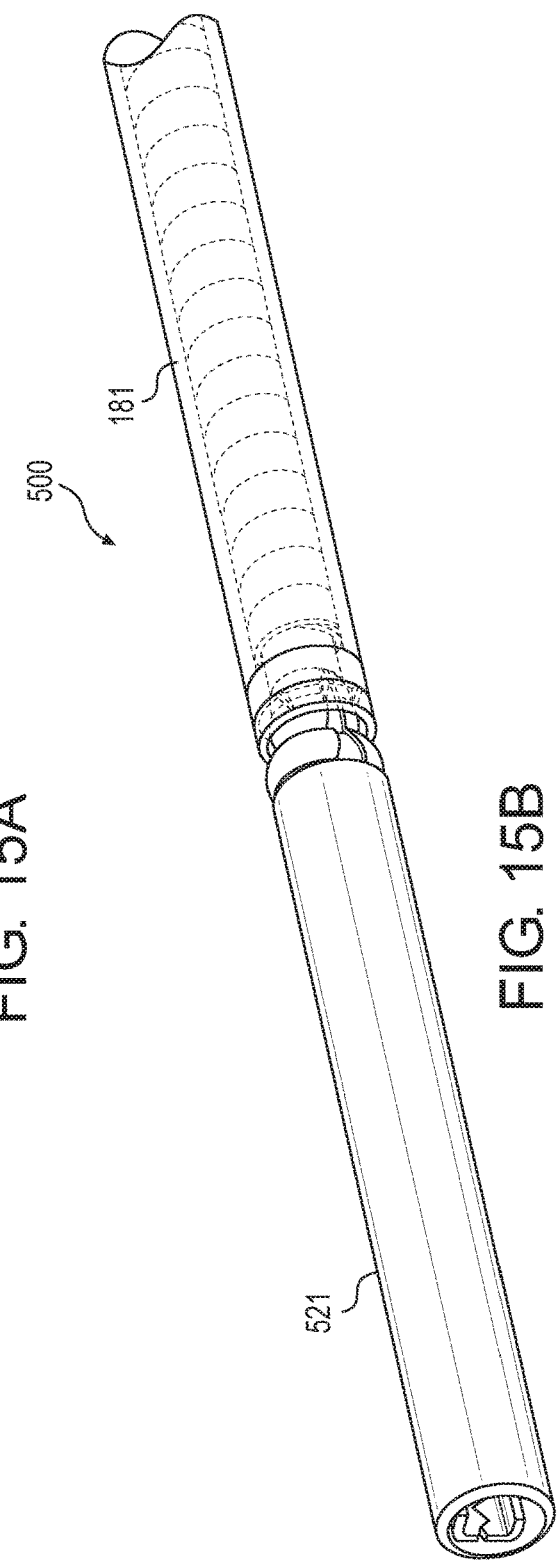

FIGS. 15A-15D show an exemplary tissue clipping system 500 including clipping device 510 releasably coupled to delivery device 530. As shown in FIGS. 15A and 15B, the clipping device 510 includes clip 511 and lock tube 521. The clipping device 510 is coupled to the delivery device 530 in FIG. 15B with the clip 511 in the closed configuration inside the channel of the lock tube 521 to facilitate delivery of the clipping device 510 to the target area in the body. The clipping device 510 may be described as being in the delivery configuration in FIG. 15B. In FIG. 15A, the clipping device 510 is still coupled to the delivery device 530, but the clip 511 has been advanced distally out of the distal end of the lock tube 521. The clip 511 is shown in the closed configuration in FIG. 15A, but would begin to expand to the open configuration once the clip 511 is advanced that far out of the lock tube 521. In other words, in FIG. 15A, the clip 511 is being deployed to the target area to shift to the open configuration to receive tissue for clipping.

Figure 15C:
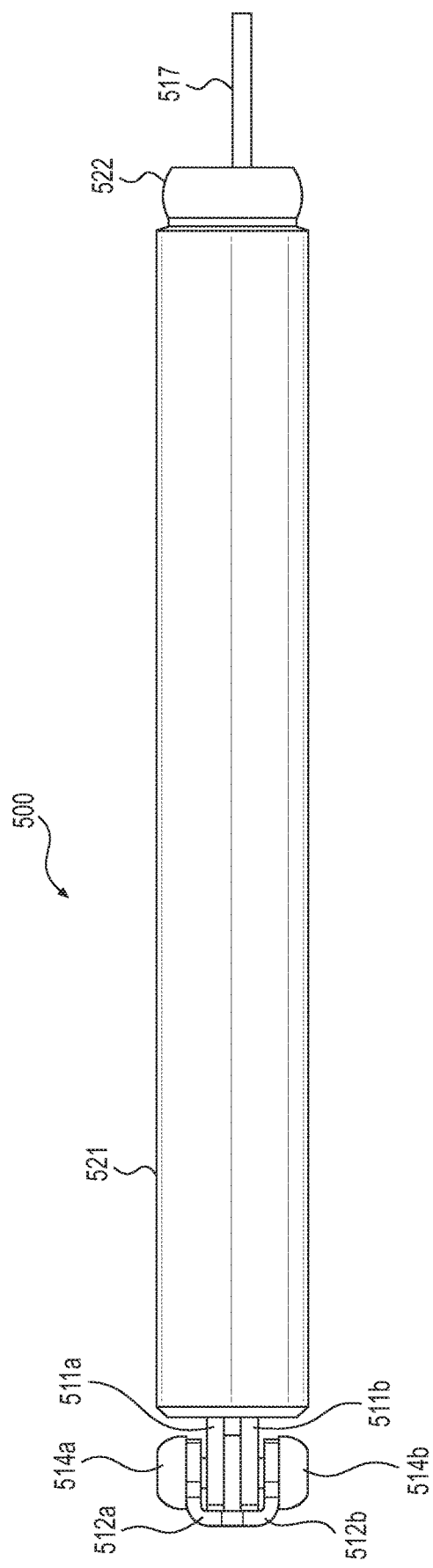
Figure 15D:
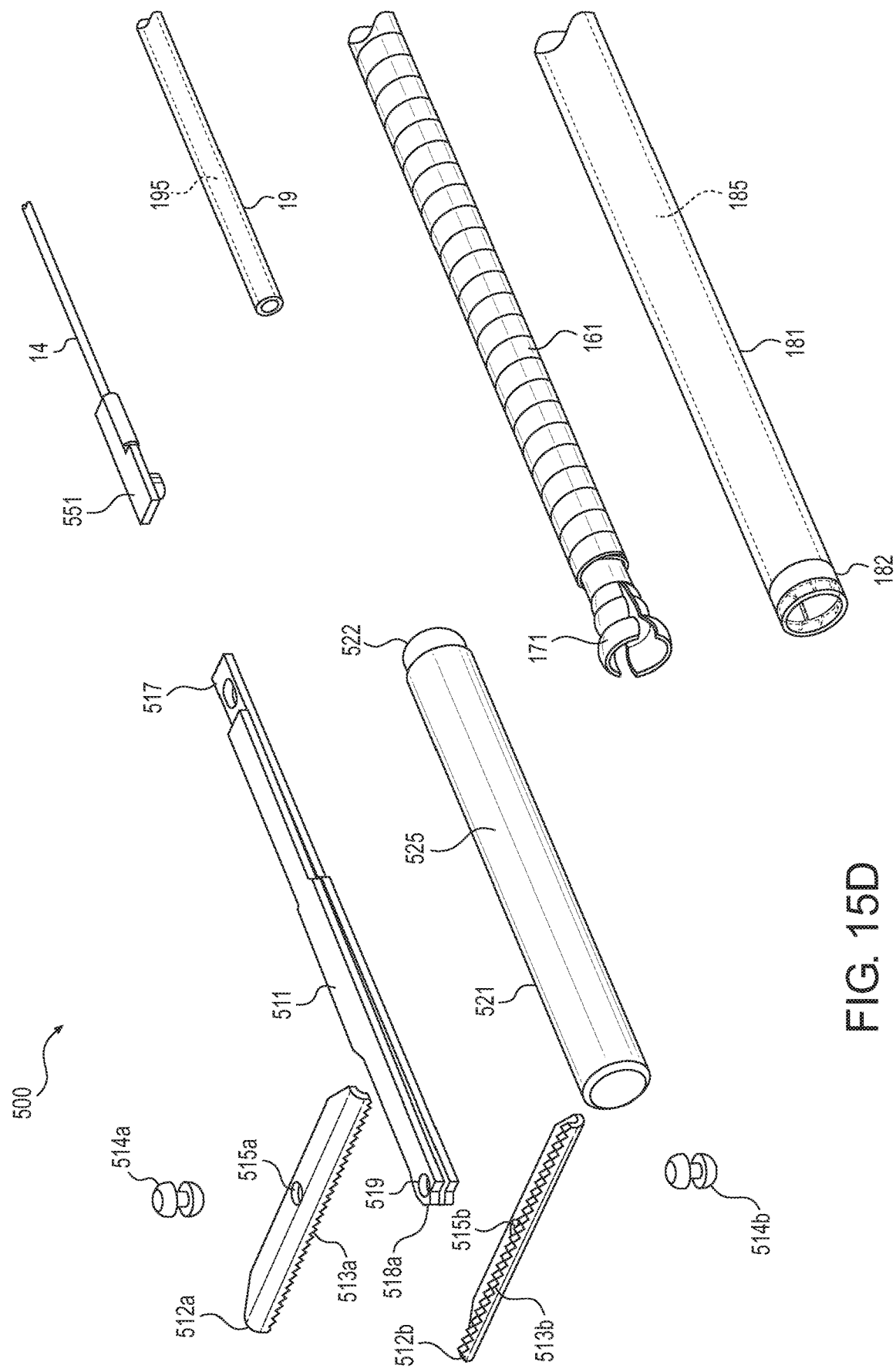

In the present embodiment, the clip 511 includes two clip arms 511a, 511b with pivotable jaws 512a, 512b coupled to the distal end, as shown in FIGS. 15C and 15D. The pivotable jaws 512a, 512b are designed to gather and clip tissue. For example, the jaws 512a, 512b may have teeth 513a, 513b (see FIG. 15D) to facilitate clipping the tissue.

Detailed view of the pivotable jaws 512 are also shown in FIGS. 10A-10F. The jaws 512a, 512b are pivotably coupled to the distal ends of the clip arms 511a, 511b. For example, in FIG. 15D, rivets 514a and 514b are used to pivotably couple the jaws 512a, 512b to the clip arms 511a, 511b. The rivet 514a extends through opening 515a in jaw 512a, and opening 519 in clip arm 511 so as to pivotably couple the jaw 512a to the clip arm 511a. Similarly, rivet 514b extends through opening 515b in jaw 512b and an opening (not shown) in clip arm 511b so as to pivotably couple the jaw 512b to the clip arm 511a. The clip 511 is not limited to the use of rivets 514 to couple the jaws 512 to the arms 511. Any other suitable connection mechanism for pivotably attaching the jaws 512 to the arms 511 may be used.

Figure 10B:
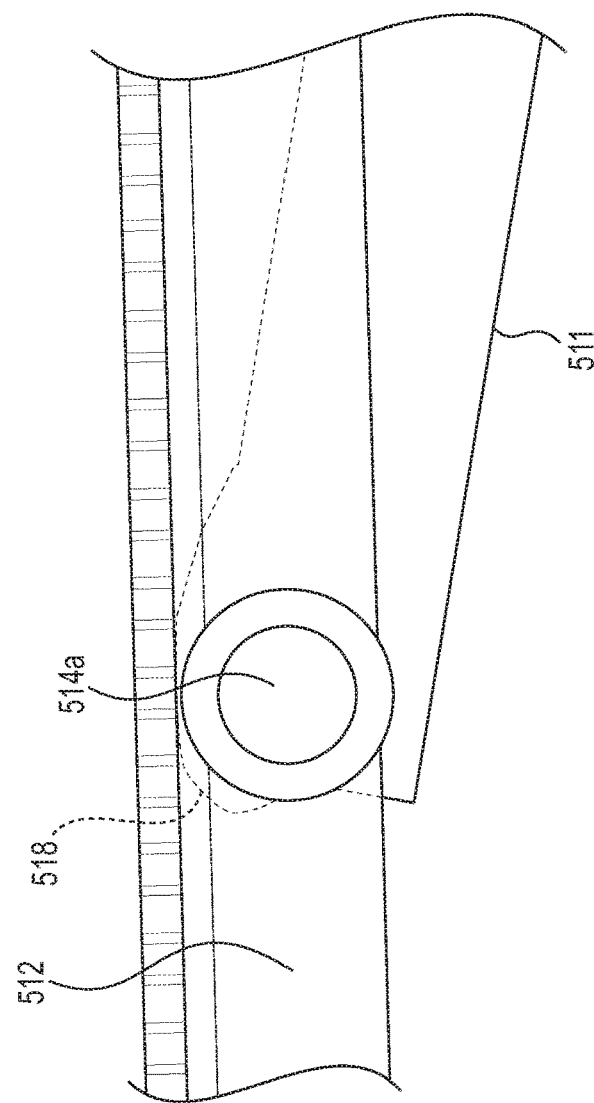
FIGS. 10A-10F show a tissue clipping device according to the disclosed embodiments.
Figure 10A:
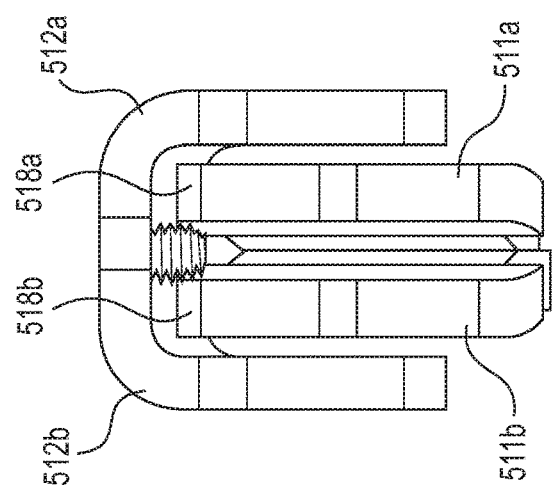
Figure 10C:
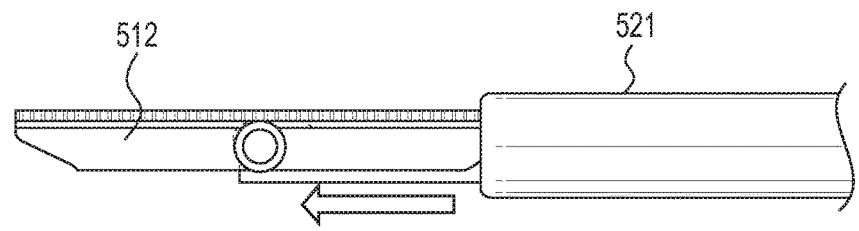

As shown in FIG. 10C, the jaws 512a, 512b are designed to be substantially parallel with the clip arms 511a, 511b so as to fit inside the channel of the lock tube 521 for delivery. The lock tube 521 is designed to radially compress the clip arms 511 into the closed configuration as shown in FIG. 15B. The clip arms 511 are designed to radially expand into the open configuration when the clip 511 is advanced in the distal direction. For example, the clip arms 511 may be stainless steel spring arms. The lock tube 521 also constrains the jaws 512a, 512b from pivoting with respect to the clip arms 511a, 511b when the jaws 512a, 512b are disposed inside the channel of the lock tube 521.

Figure 10D:
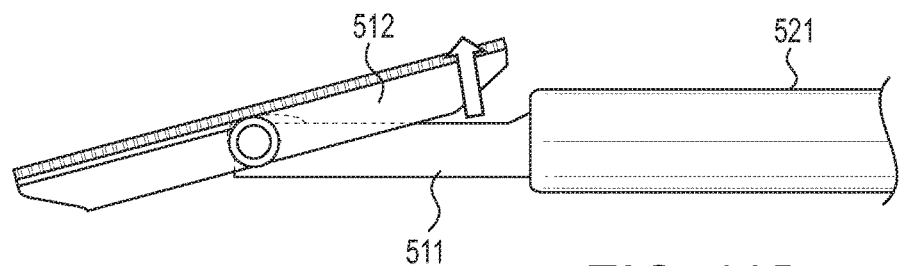
Figure 10E:
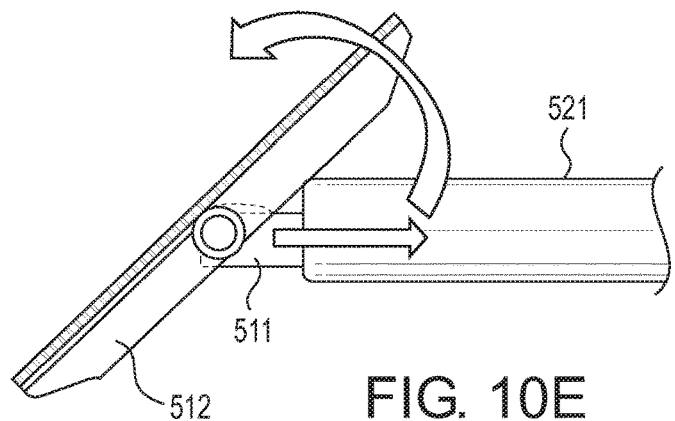
Figure 10F:
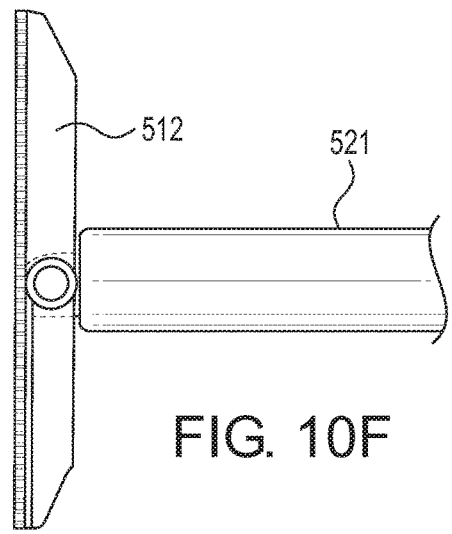

When the clip 511 is advanced in a distal direction through the lock tube 521 and the jaws 512a, 512b are released from the constrain of the lock tube 521, the jaws 512a, 512b begin to automatically pivot with respect to the arms 511a, 511b, as shown in FIGS. 10C and 10D. A curved surface or bump 518a, 518b may be provided on the distal end of the arms 511a, 511b, as shown in FIGS. 10A and 10B, so as to create a preload for pivoting the jaws 512a, 512b. To fully pivot the jaws 512a, 512b with respect to the clip arms 511a, 511b, the clip can be retracted a short distance in a proximal direction such that the jaws 512a, 512b abut against the distal end of the lock tube 521, as shown in FIGS. 10E-10F. As shown in FIG. 10F, the jaws 512a, 512b are fully pivoted and ready to open. Then, the clip 511 can be advanced in a distal direction to shift the clip 511 from the closed configuration to the open configuration for receiving tissue between the jaws 512a, 512b, as discussed above. The lock tube 521 is designed to be advanced in a distal direction with respect to the clip 511 such that the wall of the lock tube 521 radially constrains the clip 511 to shift the clip 511 from the open configuration to the closed, tissue clipping configuration such that tissue is clipped between jaws 512a, 512b. Then, the clip 511 can lockingly engage a locking connector on the lock tube 521 to lock the clip 511 including jaws 512a, 512b into the closed, tissue clipping configuration, after which the clipping device 510 can be detached from the delivery device 530 and the delivery device can be removed from the body, leaving the clipping device 510.

The jaws 512a, 512b facilitate clipping larger areas of tissue. If desired, multiple clips with the jaws 512a, 512b can be provided close together in a side-by-side manner to eliminate gap and reduce bleeding or leakage of bodily fluids.

The delivery device 530 includes a control member 14, an inner liner 19, an insertion member 161, and an outer sheath 181 (see FIG. 12F). The outer sheath 181 is designed to surround an outer surface of the insertion member 161, but may not cover the clipping device 510 (see FIGS. 12A and 12B). The control member 14 is designed to be received within a channel 195 of the inner liner 19, which is designed to be received within a channel 165 of the insertion member 161, which in turn is designed to be received within a channel 185 of the outer sheath 181.

The clipping device 510 is releasably coupled to the delivery device 530 for delivery and deployment of the clipping device 510. In particular, with reference to FIG. 15D, a proximal end 517 of the clip 511 is designed to be coupled to a hook connector 551 on the distal end of the control member 14, and a proximal end 522 of the lock tube 521 is designed to be coupled to a socket connector 171 on the distal end of the insertion member 161. The hook connection between hook connector 551 and the proximal end 517 of the clip 511 is the same as that discussed above with respect to hook connector 151, and thus, is not repeated here. Similarly, the ball-and-socket connection between the ball-like proximal end 522 of the lock tube 521 and the socket connector 171 is the same as that discussed and thus is not repeated here.

Figure 16A:
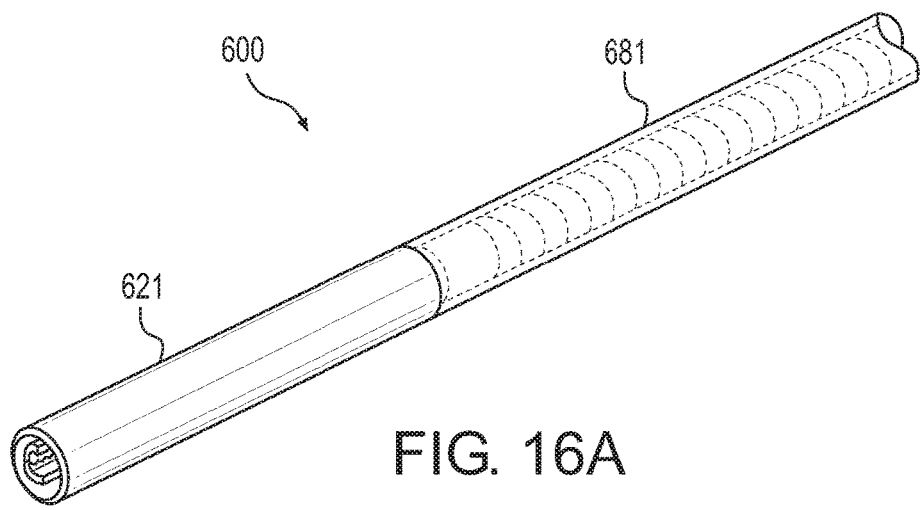
Figure 16B:
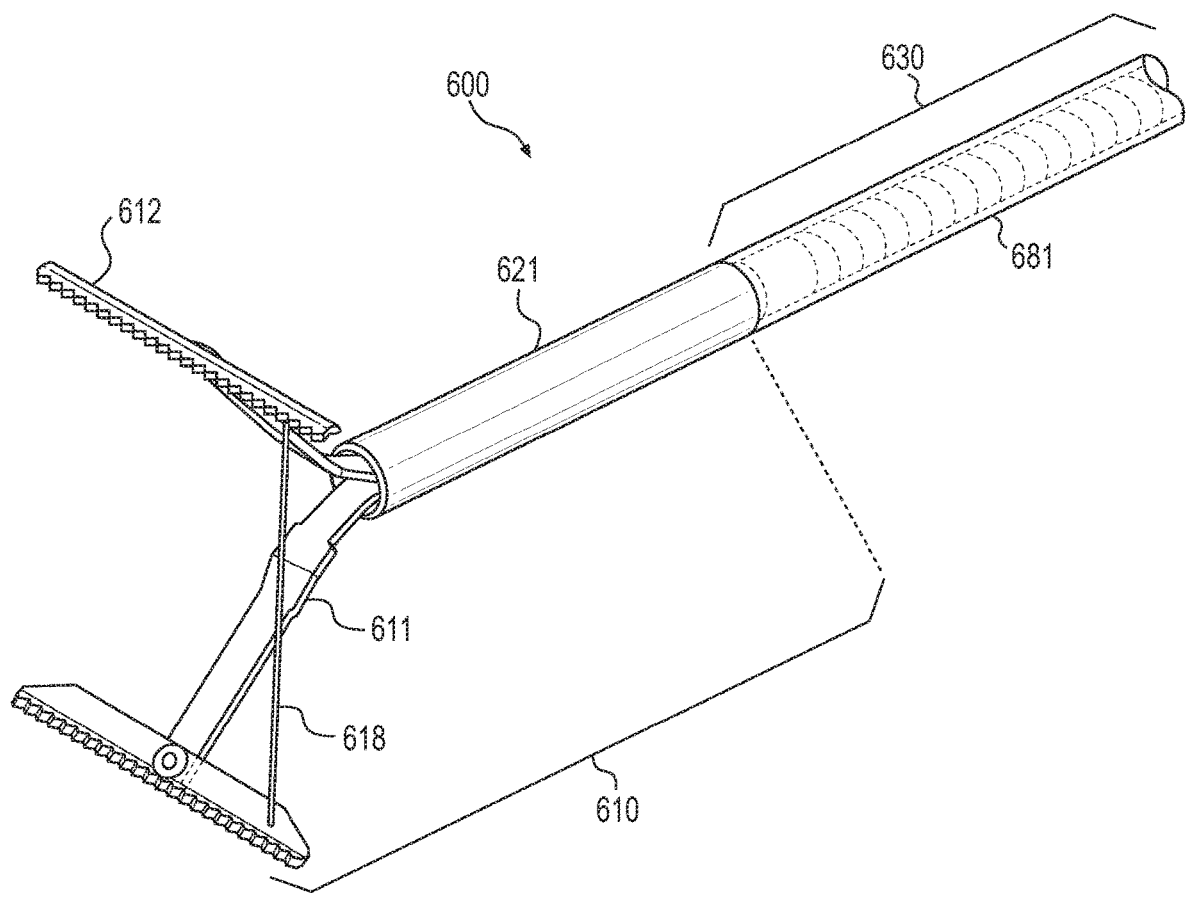
Figure 16C:
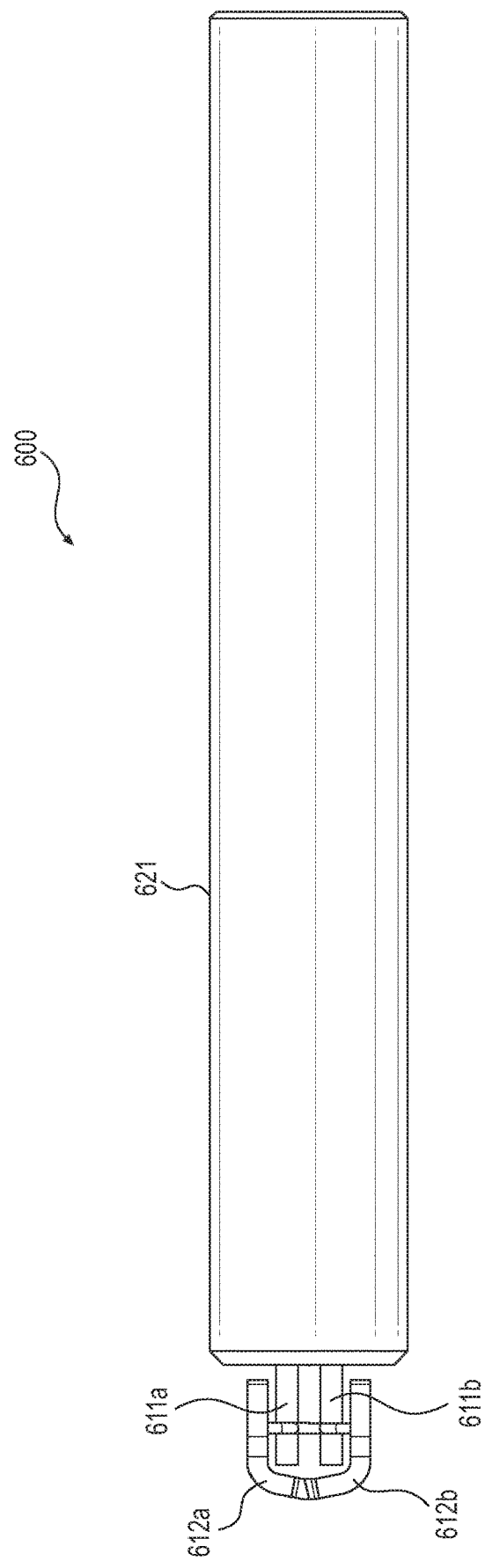

FIGS. 16A-16J show an exemplary tissue clipping system 600 including a clipping device 610 releasably coupled to delivery device 630. As shown in FIGS. 16A and 16B, the clipping device 610 includes clip 611 and lock tube 621. The clipping device 610 is coupled to the delivery device 630 in FIG. 16A with the clip 611 in the closed configuration inside the channel of the lock tube 621 to facilitate delivery of the clipping device 610 to the target area in the body. The clipping device 610 may be described as being in the delivery configuration in FIG. 16A. In FIG. 16B, the clipping device 610 is still coupled to the delivery device 630, but the clip 611 has been advanced distally out of the distal end of the lock tube 621 such that the clip arms 611 radially expand into the open configuration. In other words, in FIG. 16B, the clip 611 is deployed to the target area and has been shifted to the open configuration to receive tissue for clipping.

Figure 16D:
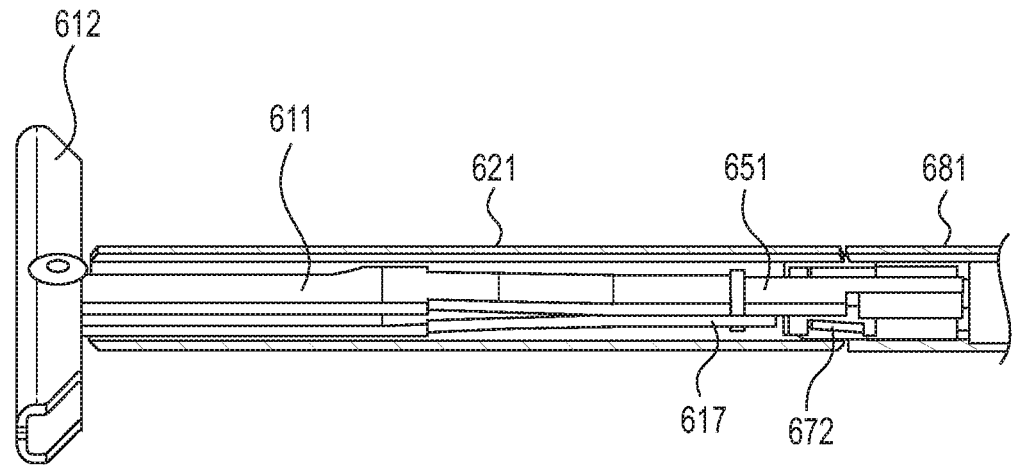
Figure 16E:
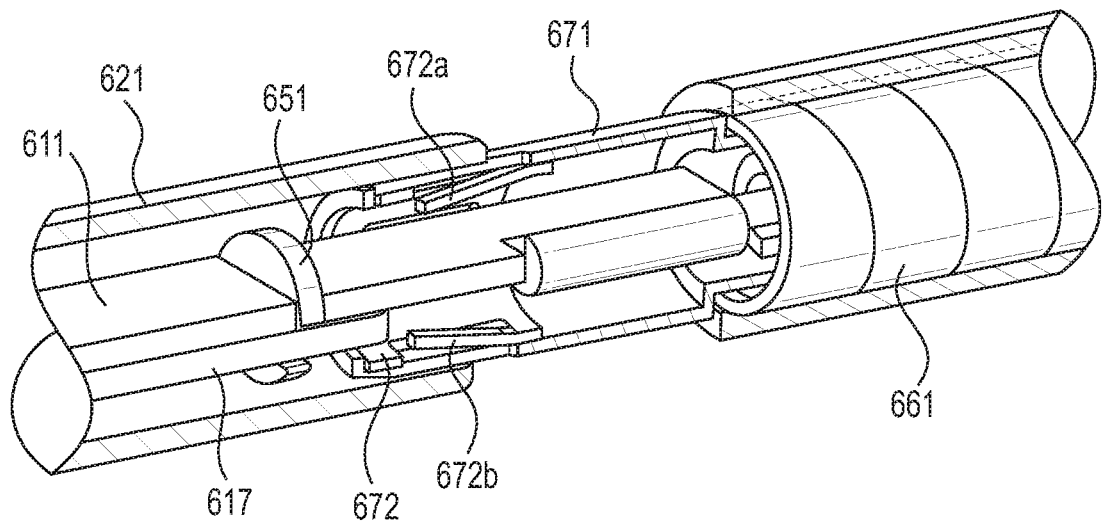
Figure 16F:
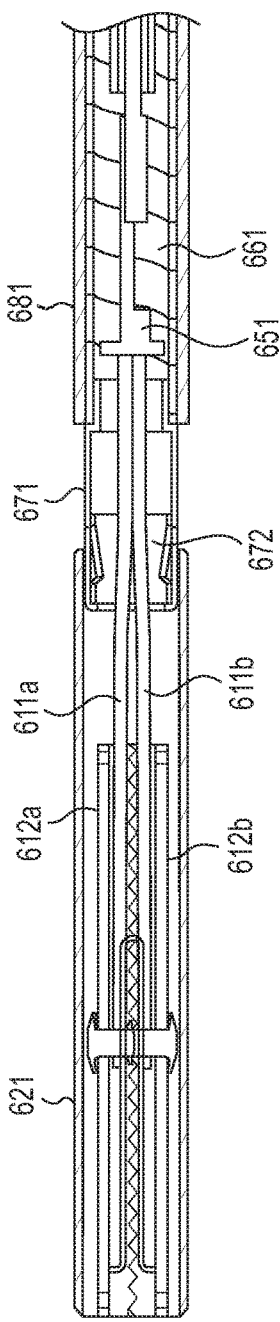
Figure 16G:
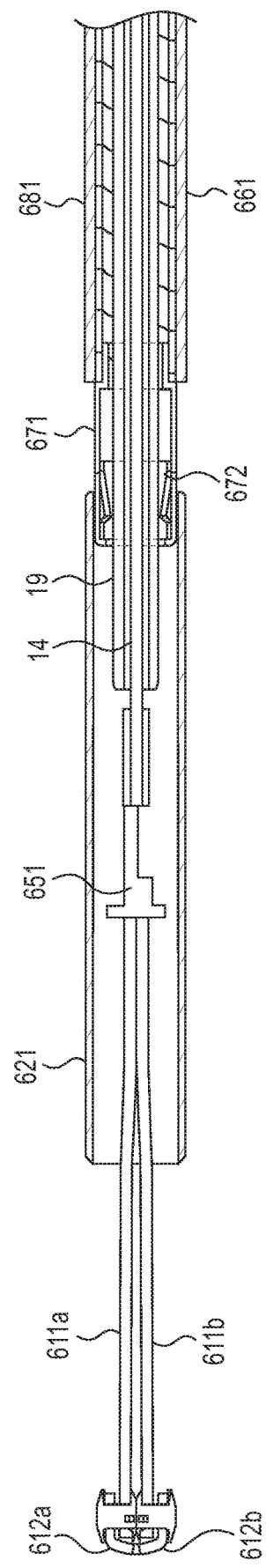
Figure 16J:
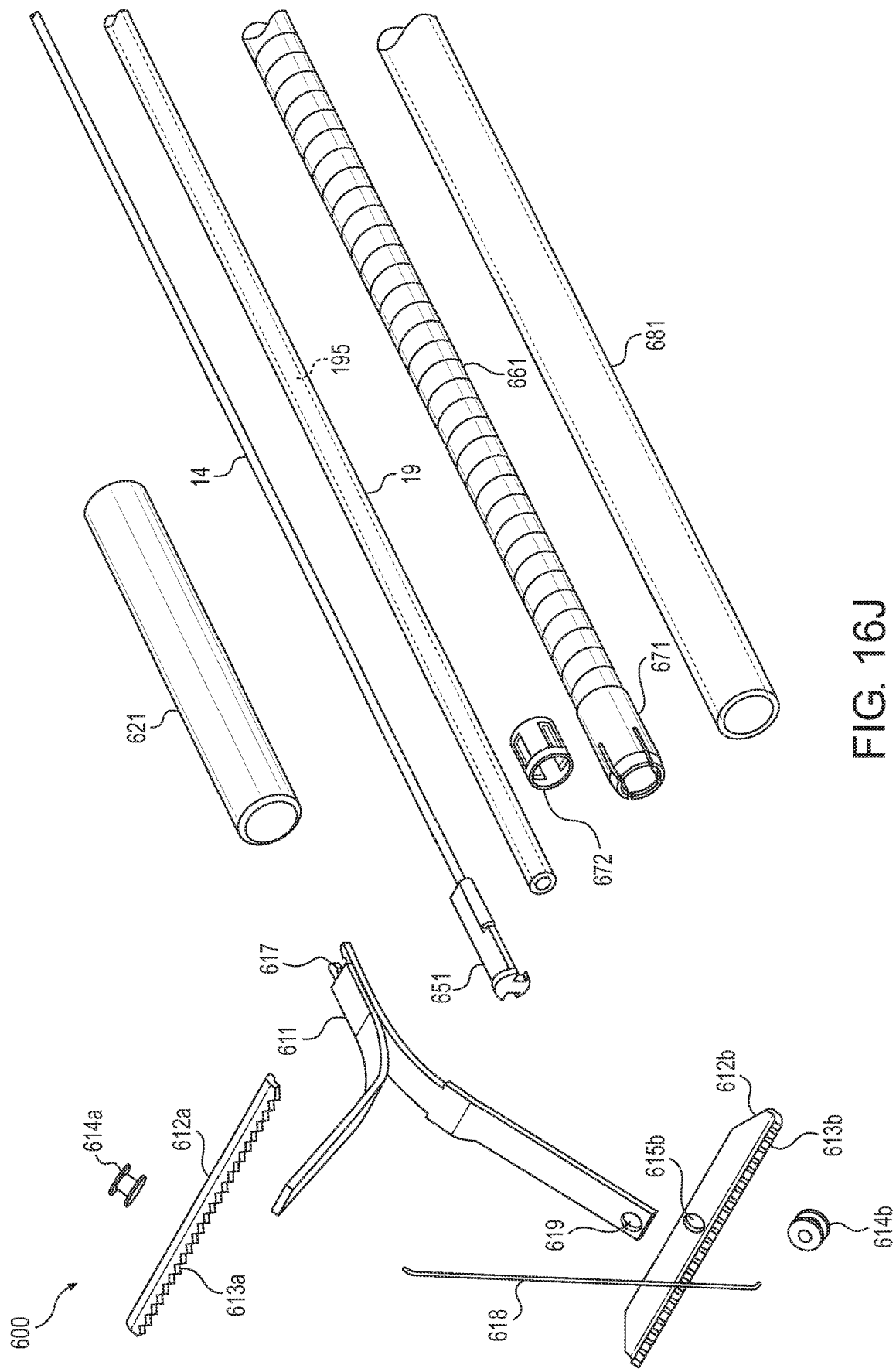

In the present embodiment, the clip 611 includes two clip arms 611a, 611b with pivotable jaws 612a, 612b coupled to the distal end, as shown in FIG. 16J. The pivotable jaws 612a, 612b are designed to gather and clip tissue. For example, the jaws 612a, 612b may have teeth 613a, 613b to facilitate clipping the tissue. The clip 611 including jaws 612a, 612b are substantially the same as clip 511 including jaws 512a, 512b except that it additionally includes tension wire 618, discussed in more detail below.

The jaws 612a, 612 b are pivotably coupled to the distal ends of the clip arms 611a, 611b. For example, in FIG. 16J, rivets 614a and 614b are used to pivotably couple the jaws 612a, 612b to the clip arms 511a, 511b. The rivet 614a extends through an opening in jaw 612a, and opening in clip arm 611a so as to pivotably couple the jaw 612a to the clip arm 611a. Similarly, rivet 614b extends through an opening 615b in jaw 612b and an opening 619 in clip arm 611b so as to pivotably couple the jaw 612b to the clip arm 611a. The clip 611 is not limited to the use of rivets 614 to couple the jaws 612 to the arms 611. Any other suitable connection mechanism for pivotably attaching the jaws 612 to the arms 611 may be used.

Detailed view of the pivotable jaws 612 are also shown in FIGS. 11A-11F. As shown in FIG. 12C, the jaws 612a, 612b are designed to be substantially parallel with the clip arms 611a, 611b so as to fit inside the channel of the lock tube 621 for delivery. The lock tube 621 is designed to radially compress the clip arms 611 into the closed configuration as shown in FIG. 16A. The clip arms 611 are designed to radially expand into the open configuration when the clip 611 is advanced in the distal direction. For example, the clip arms 611 may be nitinol spring arms. The lock tube 621 also constrains the jaws 612a, 612b from pivoting with respect to the clip arms 611a, 611b when the jaws 612a, 612b are disposed inside the channel of the lock tube 521.

Figure 11B:
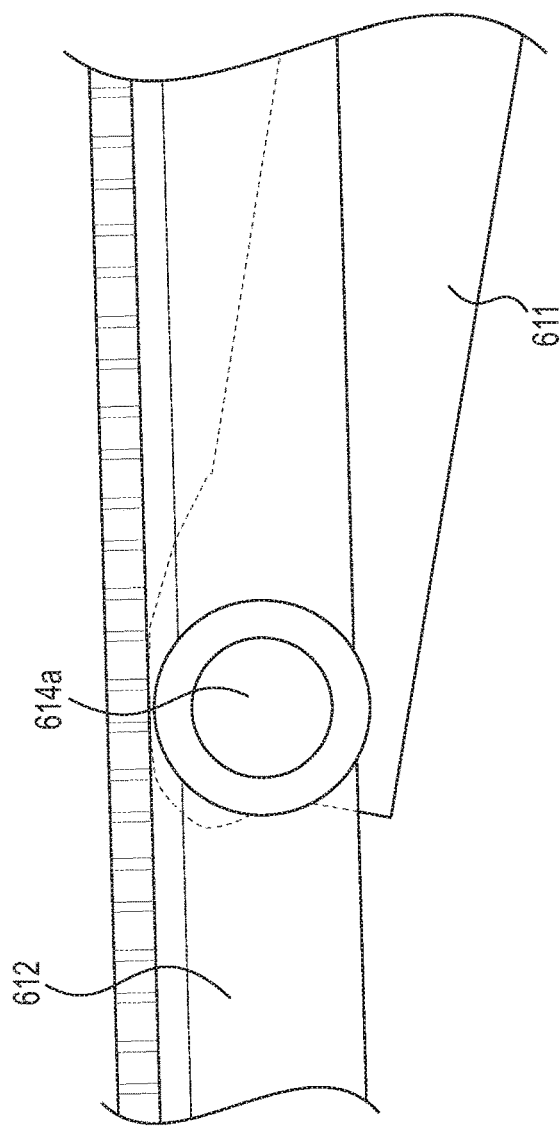
FIGS. 11A-11F show a tissue clipping device according to the disclosed embodiments.
Figure 11A:
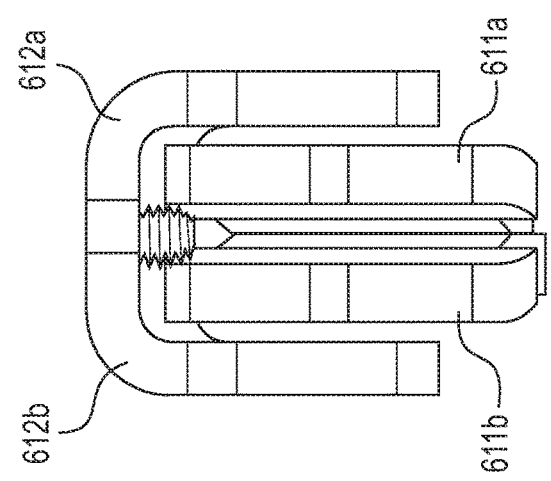
Figure 11C:
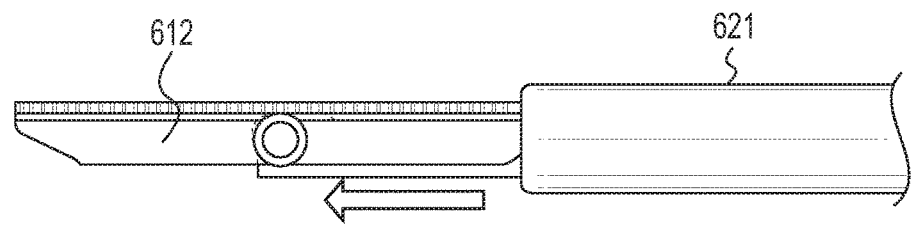
Figure 11D:
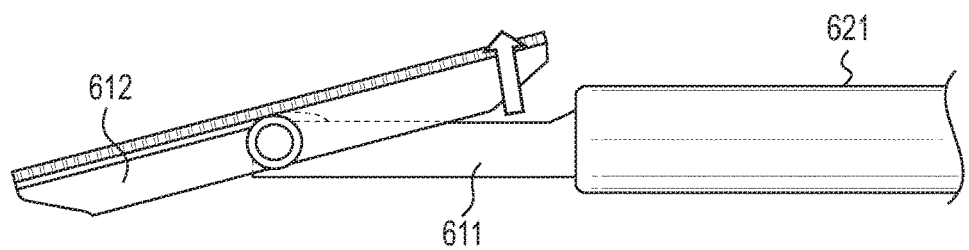

Like jaws 512 discussed above, jaws 612a, 612b are designed to automatically pivot due a preload on the arms 611a, 611b, as shown in FIGS. 11C and 11D. However, it is not necessary to retract clip 611 so that the jaws 612a, 612b abut against the distal end of the lock tube 621 to completely pivot the jaws 612 with respect to the arms 611, as discussed above with respect to clip 511. Instead, the jaws 612a, 612b are designed to pivot with respect to arms 611a, 611b when the clip 611 is advanced in the distal direction to tension on the wire 618. That is, jaws 612a, 612b should fully pivot with respect to the arms 611a, 611b by advancing the clip 611 in the distal direction due to tension on the wire 618.

Figure 11E:
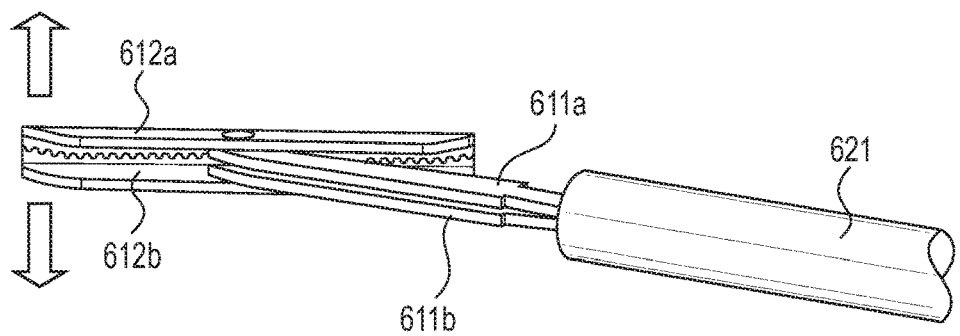
Figure 11F:
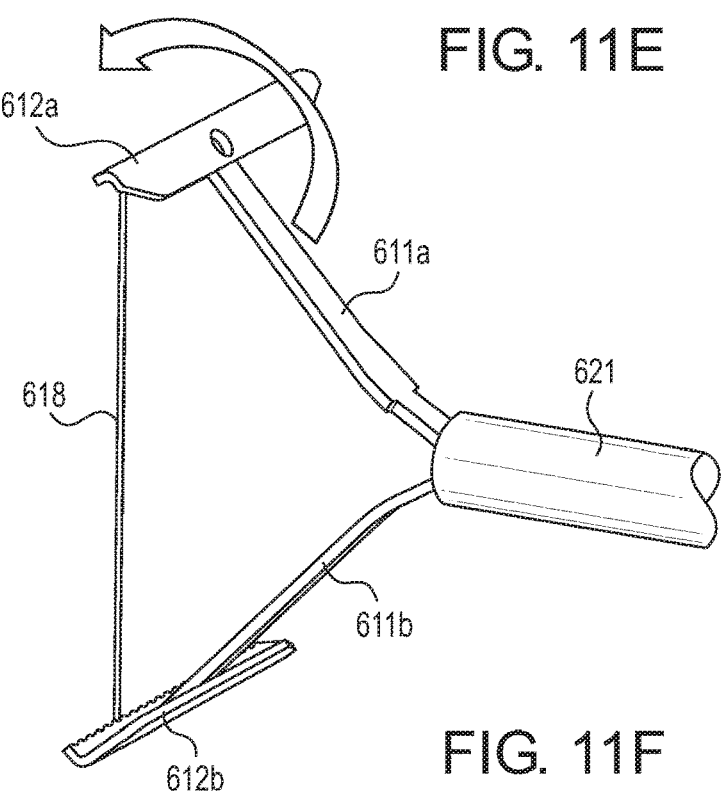

Therefore, jaws 612a, 612b should be fully pivoted as the jaw arms 611a, 611b are fully open, as shown in FIGS. 11E and 11F.

As shown in FIG. 11F, the jaws 612a, 612b are fully pivoted and in the open configuration for receiving tissue between the jaws 612a, 612b, as discussed above. After the jaws 612a, 612b have been positioned for receiving tissue, the lock tube 621 can be advanced in the distal direction with respect to the clip 611 to radially constrain the clip arms 611a, 611b so as to shift the clip 611 from the open configuration to the closed, tissue clipping configuration such that tissue is clipped between jaws 612a, 612b. For example, a detailed view of the clip 611 in the closed configuration is shown in FIG. 16D. Then, the clip 611 can lockingly engage a locking connector on the lock tube 621 to lock the clip 611 including jaws 612a, 612b into the closed, tissue clipping configuration, after which the clipping device 610 can be detached from the delivery device 630 and the delivery device can be removed from the body, leaving the clipping device 610.

The jaws 612a, 612b facilitate clipping larger areas of tissue. If desired, multiple clips with the jaws 612a, 612b can be provided close together in a side-by-side manner to eliminate gap and reduce bleeding or leakage of bodily fluids.

The delivery device 630 includes a control member 14, an inner liner 19, an insertion member 661, and an outer sheath 681 (see FIG. 16J). The outer sheath 681 is designed to surround an outer surface of the insertion member 661, but may not cover the clipping device 610 (see FIGS. 16A and 16B). As shown in the cross-sectional views of FIGS. 16D-16I, the control member 14 is received within a channel 195 of the inner liner 19, which is received within a channel 665 of the insertion member 661, which in turn is received within a channel 685 of the outer sheath 681.

The clipping device 610 is releasably coupled to the delivery device 630, as shown in FIGS. 16A, 16B, and 16D-16I for delivery and deployment of the clipping device 610. In particular, a proximal end of the clip 611 includes a fork connector 617 that is designed to releasably connect to clip connector 651 on the distal end of the control wire. A proximal end of the lock tube 621 is also releasably coupled with a lock tube connector 671 on the distal end of the insertion member 661 via an internal slider 672.

The fork connection between fork connector 617 and clip connector 651 is the same as that discussed above with respect to fork connector 312 and clip connector 351 and thus is not repeated.

Figure 6C:
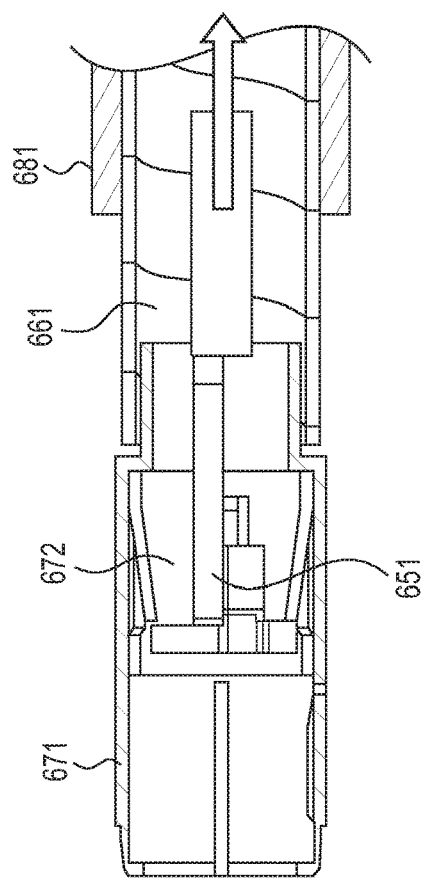
Figure 6C:
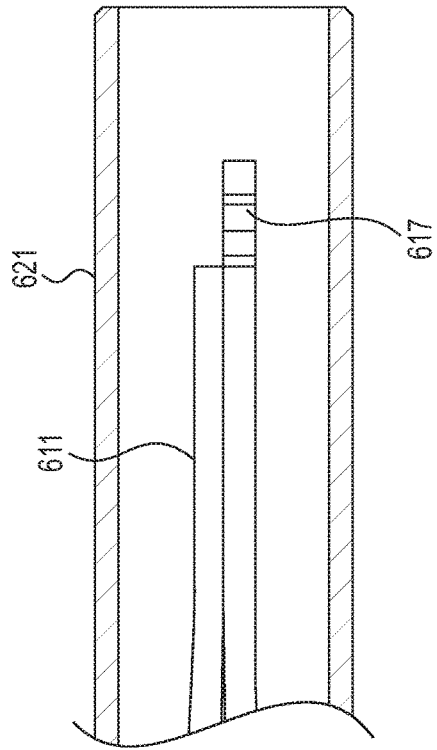

Detailed view of the internal slider connection between the lock tube 621 and the insertion member 661 are shown in FIGS. 6A-6C and FIGS. 16E-16I. In the internal slider connection, the lock tube connector 671 on the distal end of the insertion member 661 frictionally grips a proximal end of the lock tube 621 by virtue of an internal slider 671. The lock tube connector 671 is spring loaded inward, but can frictionally grip an interior surface of the lock tube 621 by virtue of the internal slider 671. As shown in FIG. 6A, the lock tube 621 is releasably held by the lock tube connector 671 including slider 672. Likewise, the clip connector 651 is held by the fork connector 617 on the proximal end of the clip 611 in FIG. 6A. The lock tube connector 671 is disengaged from the lock tube 621 by retracting the control member 14 in the proximal direction. Retraction of the control member 14 disengages the clip connector 651 and fork connector 617 as discussed above. Continued retraction of the control member 14 pulls the clip connector 651 through an inner channel of the lock tube connector 671 and internal slider 672 such that the clip connector 651 abuts against arms 672a, 672b of the internal slider 672 so as to pull the internal slider 672 in a proximal direction with respect to the lock tube connector 671, as shown in FIG. 6B. When the internal slider 672 is moved to the proximal end of the lock tube connector 671, the lock tube connector 671, which is spring loaded inward, move radially inward to release such that they no longer frictionally grip the interior of the lock tube 621. Then, continued retraction of the control member 14 will move the lock tube connector 671 in the proximal direction out of the end of the lock tube 621 such that the lock tube 621 is fully disengaged from the lock tube connector 671 of the insertion member 661, as shown in FIG. 6C. The lock tube connector 671 and internal slider 672 are compatible with the fork connector 312 (which is the same as 617), as well as the alternative fork connector 751, discussed below.

The clipping system 600 including clipping device 610 enable not only clipping of large perforations, defects, and fistulas, but also involve a simple interaction and the clip device 610 may be shorter.

As discussed above, the proximal end of the clip may be releasably coupled to the clip connector via a hook connector, fork connector, or any other suitable releasable connection. The hook connector 151 of FIGS. 2A-2C, and the fork connector 312 of FIGS. 3A-3C are discussed above.

Figure 4:
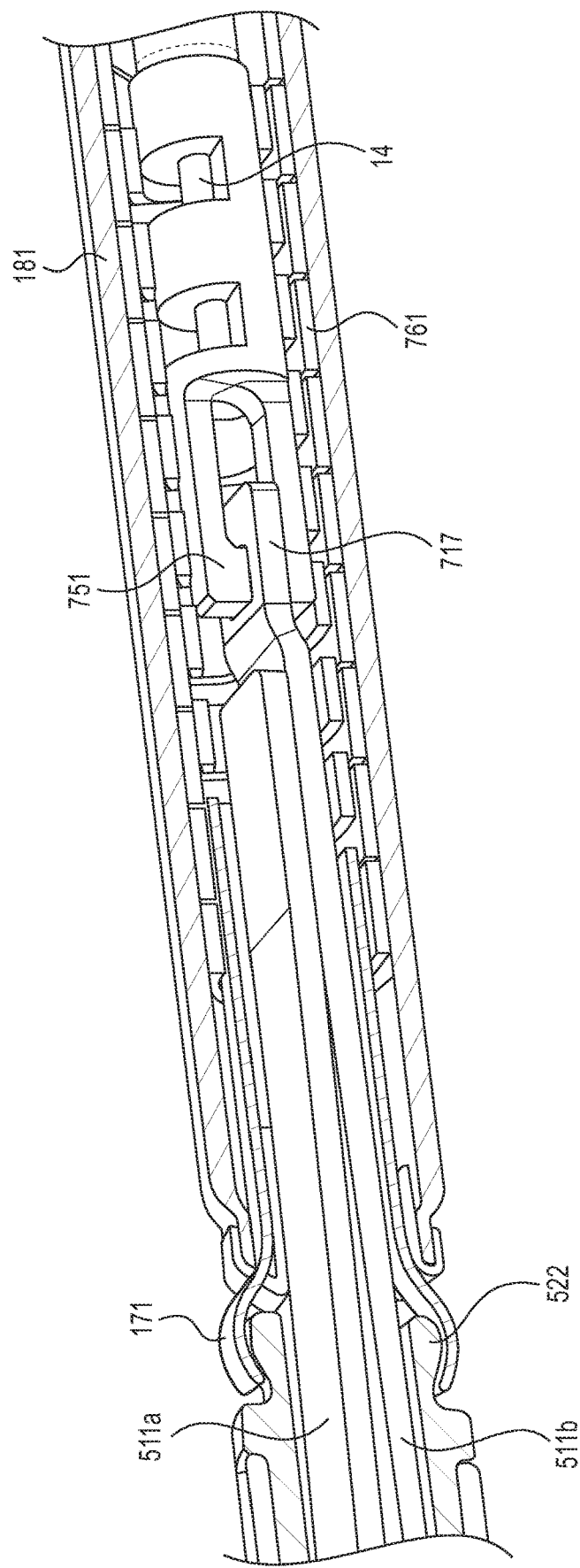
FIG. 4 shows a releasable clip connection mechanism according to the disclosed embodiments.

FIG. 4 shows another exemplary clip releasable connection between the clip connector on the distal end of the insertion member and the proximal end of the clip. FIG. 4 shows an alternative fork connection in which a fork connector 751 is formed on the distal end of the control member 14, and the catch 717 is formed on the proximal end of the clip arms 511a and 511b of the clip 511. This clip connection is designed to be released in the same manner as that discussed above with respect to FIGS. 3A-3C. For example, once the clip 511 is locked to the lock tube 521, the control member 14 can be retracted in the proximal direction to release the catch 717 on the proximal end of the clip 511 from the fork connector 751, which similarly has arms that are spreadable in response to proximal retraction of the control member 14. The fork connector 751 is similarly designed to release the catch 717 of the clip 511 before the lock tube 521 is released from the lock tube connector 171. Although the alternative fork connector 751 and catch 717 are illustrated on pivotable jaw clip 511, the alternative fork connection may be used with any of the embodiments disclosed herein.

As discussed above and shown in FIGS. 5A-5C, 6A-6C, 7A-7D, and 8A-8E, the proximal end of the lock tube may be releasably coupled to the lock tube connector of the insertion member via a ball and socket, frictional slider, wedge jaws, or break-away connector, or any other suitable releasable connector.

Figure 9A:
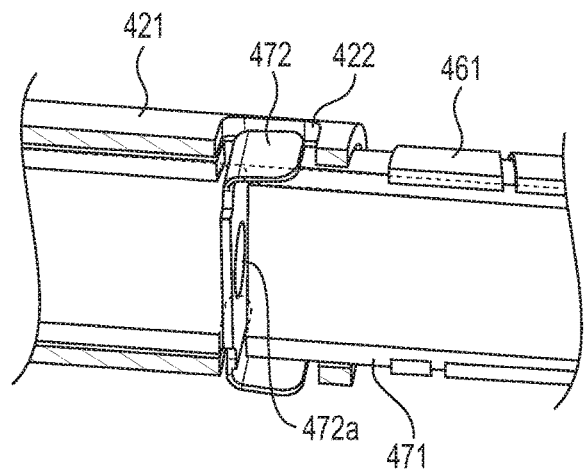
FIGS. 9A-9C show a releasable lock tube connection mechanism according to the disclosed embodiments.
Figure 9B:
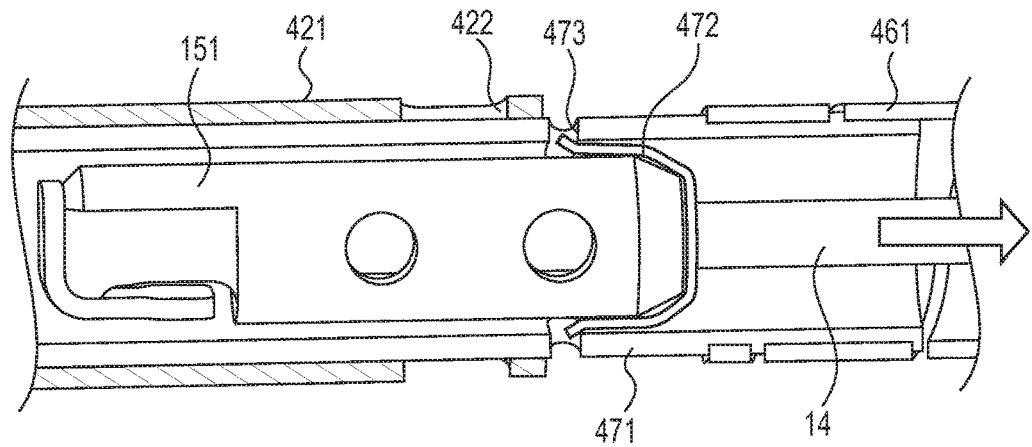
Figure 9C:
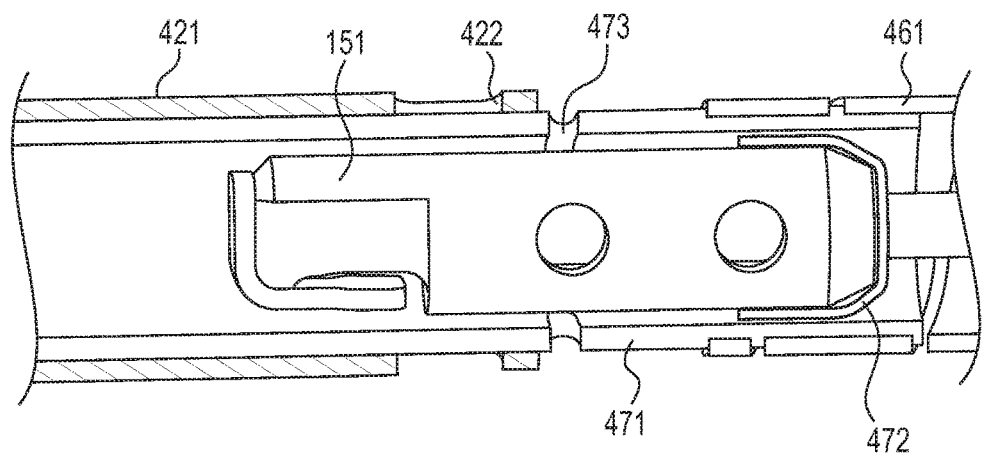

FIGS. 9A-9C shown an alternative releasable lock tube connector using a bended sheet connection. In FIGS. 9A-9C, the lock tube 421 is releasably coupled to the insertion member 461 via a bended sheet connector 472. As shown in FIG. 9A, the bended sheet connector 472 extends through an opening 473 in a distal end 471 of the insertion member 461, and an opening 422 in the proximal end of the lock tube 421. The bended sheet connector 472 is bent over both the distal end 471 of the insertion member 461 and the proximal end of the lock tube 421 to hold the insertion member 461 and the lock tube 421 together. The control member 14 extends through an opening 472a in the bended sheet so as to be able to move in the distal and proximal directions relative to the bended sheet connector 472. The control member 14 includes hook connector 151 on its distal end. Although not shown in FIGS. 9A-9C, the hook connector 151 is engaged with a proximal end 114 of the clip 111, as discussed above. The hook connector 151 has a larger outer diameter than that of the control member 14 and thus is not able to move through the opening 472a in the bended sheet 472. To disengage the bended sheet connector 471 from the lock tube 421, the control member 14 is retracted in the proximal direction such that the hook connector 151 abuts against a distal surface of the bended sheet connector 472 and deforms the bended sheet 472, as shown in FIG. 9B. The hook connector 151 pushes the bended sheet 472 out of opening 422 in the proximal end of the lock tube 421 and opening 473 in the distal end portion 471 of the insertion member 461, as shown in FIGS. 9B and 9C. As a result, the lock tube 421 is disengaged from the distal end portion 471 of the insertion member 461. Although the bended sheet connector 472 is illustrated with the radial arms clip 411, and the hook connector 151, the bended sheet connector 472 may be used with any of the embodiments disclosed herein.

As mentioned above, the clip is designed to lockingly engage the lock tube to lock the clip to the lock tube in the closed, tissue-clipping configuration. For example, the clip may include a first connector designed to engage a second connector comprised by the lock tube to lock the clip in the closed configuration. The first connector comprised by the clip is disposed within the channel of the lock regardless of whether the clip is in the open configuration or the closed configuration. Exemplary locking mechanisms and structures are shown in FIGS. 17A-17D and 18A-18E and discussed below.

Figure 17A:
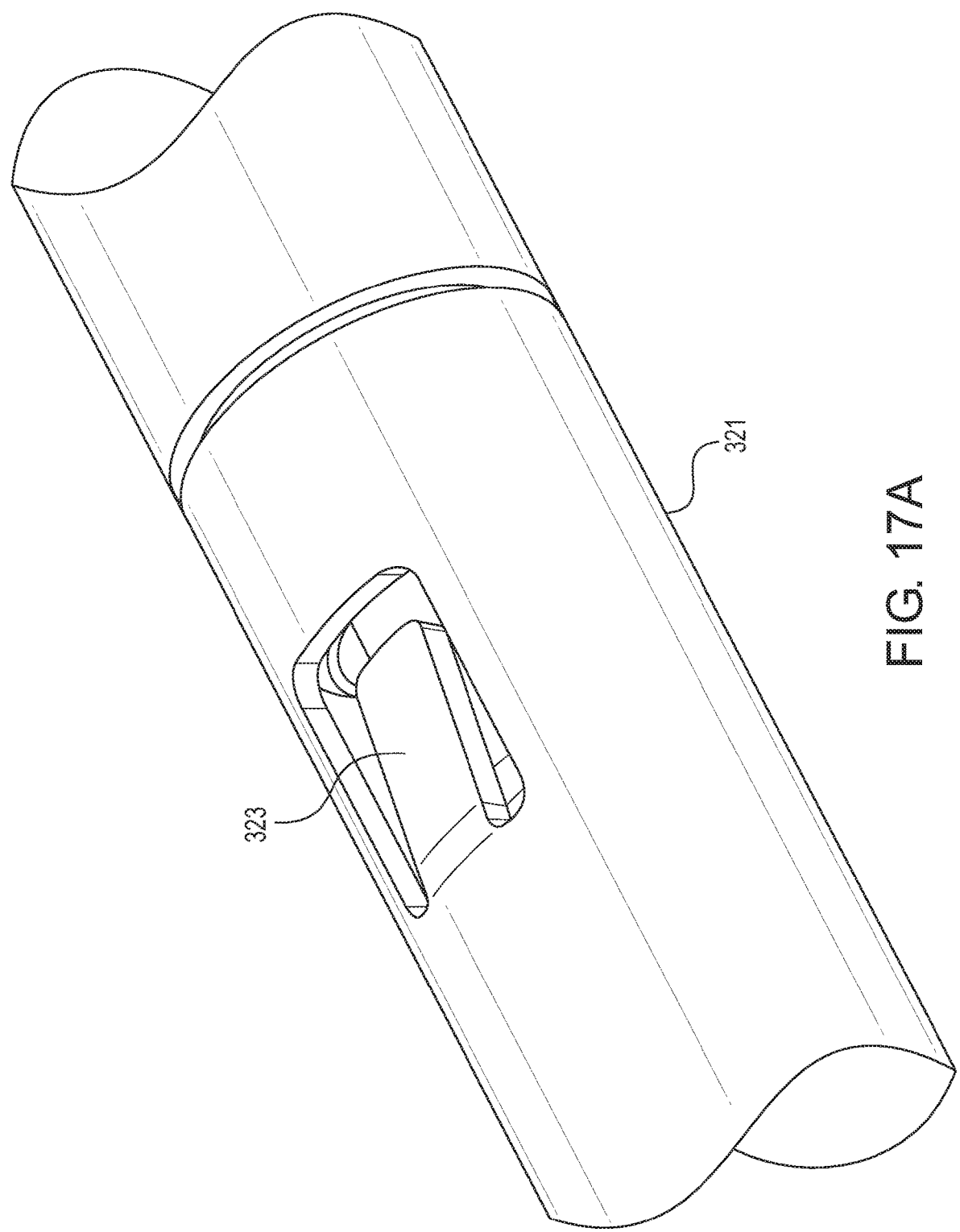
FIGS. 17A-17D show a tissue clipping device locking mechanism according to the disclosed embodiments.
Figure 17B:
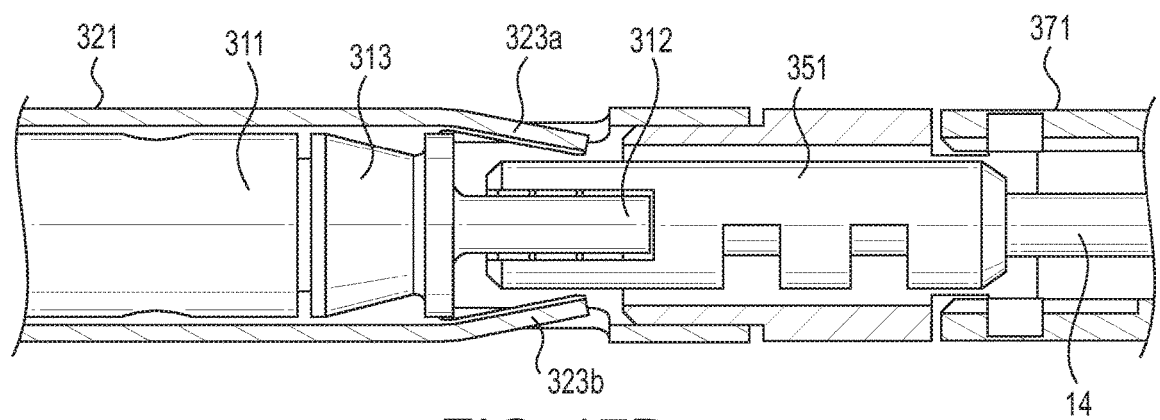
Figure 17C:
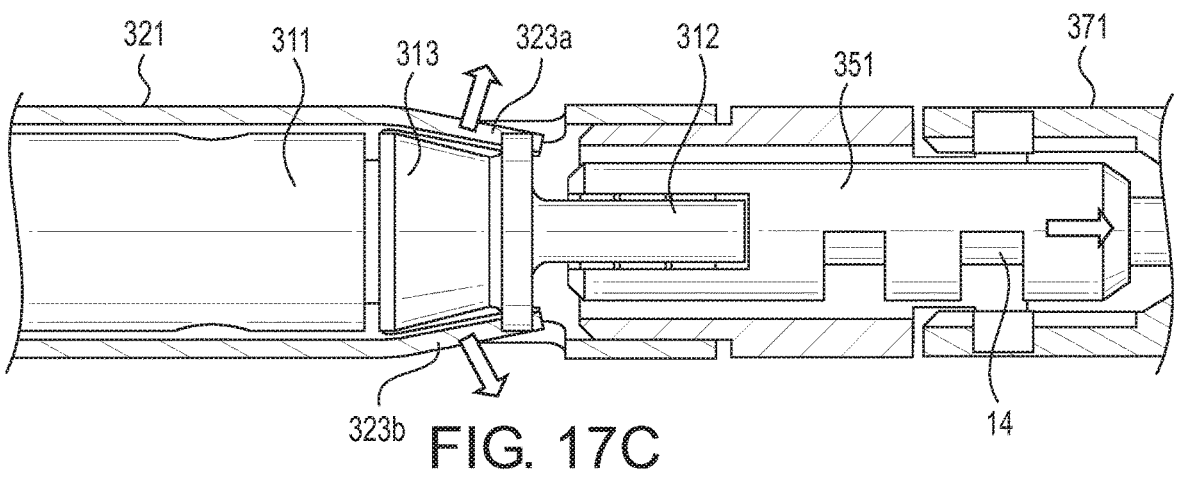
Figure 17D:
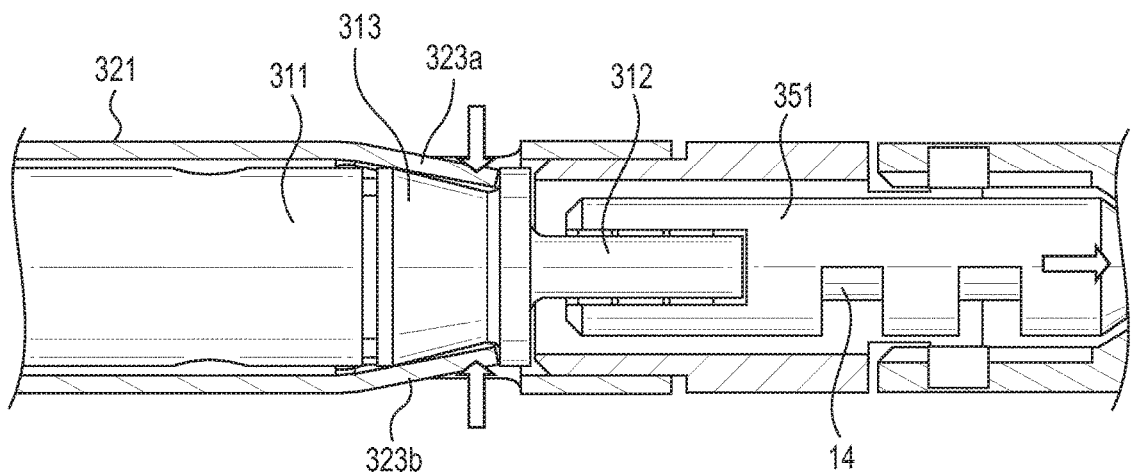

FIGS. 17A-17D show an exemplary locking mechanism for locking any of the radial clip arm structures to the lock tube in the closed, tissue clipping configuration. FIG. 17A shows an exploded view of lock tube 321 in which the wall of the lock tube 321 includes a locking tab 323. As shown in FIG. 17B, the clip 311 includes a clip connector 313 coupled near a proximal end of the clip 311. For example, the clip connector 313 may be welded to near a proximal end of the clip 311. The clip 311 is designed to slide distally and proximally with respect to the lock tube 321 while the clip connector 313 is on the distal side of the locking tabs 323a, 323 of the lock tube 321. After the clip 311 has been deployed to clip tissue, the clip 311 can be locked to the lock tube 321 by retracting the control member 14 in the proximal direction to move the clip 311 in the proximal direction with respect to the lock tube 321. As a result of the retraction, the clip connector 313 will pass through the locking tabs 323a, 323b of the lock tube 321. As shown in FIG. 17C, the locking tabs 323a, 323b are designed to expand or deform radially outward to permit the clip connector 313 to pass there through. Then, the locking tabs 323a, 323b snap closed (e.g., the tabs 323a, 323b move radially inward back toward their original position) to lock the clip 311 to the lock tube 321, as shown in FIG. 17D. As a result, the clip 311 is locked in the closed, tissue-clipping configuration. Then the clipping device can be detached from the delivery device, as discussed above. The locking mechanism shown in FIGS. 17A-17D can be used with any of the radial clip arm structures (e.g., 111, 211, or 311) discussed above.

Figure 18A:
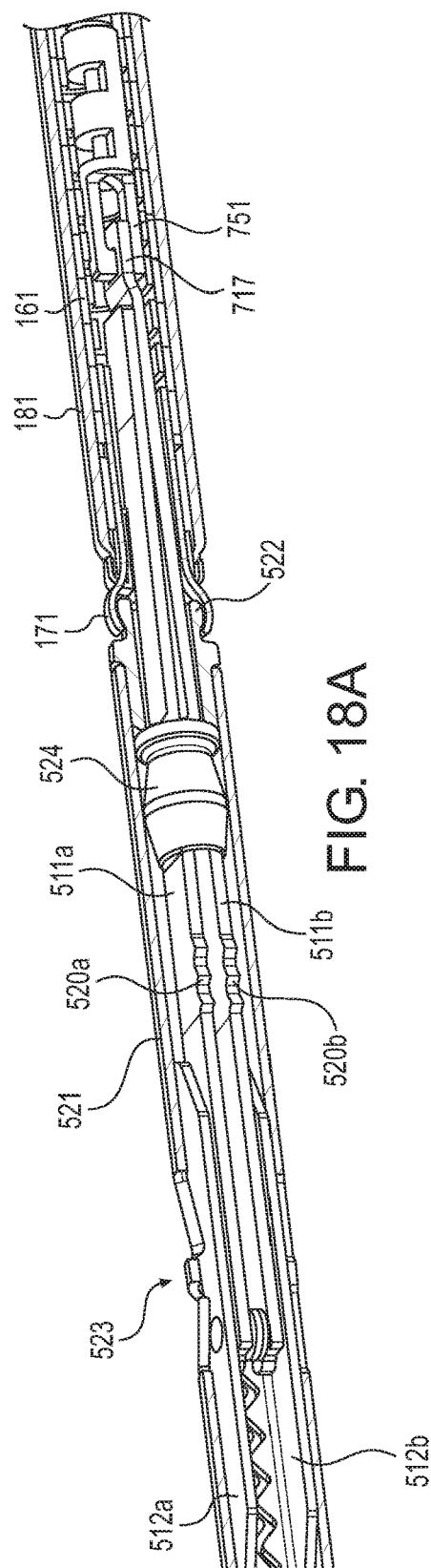

FIGS. 18A-18E show an exemplary locking mechanism for locking any of the pivotable jaw clip arm structures to the lock tube in the closed, tissue-clipping configuration. FIG. 18A shows a cross-sectional view of clipping system 500 in which the lock tube 521 includes locking connector 523, the clip arms 511a, 511b each include locking teeth 520a, 520b, and the clipping device 511 including a locking slider 524.

Figure 18B:
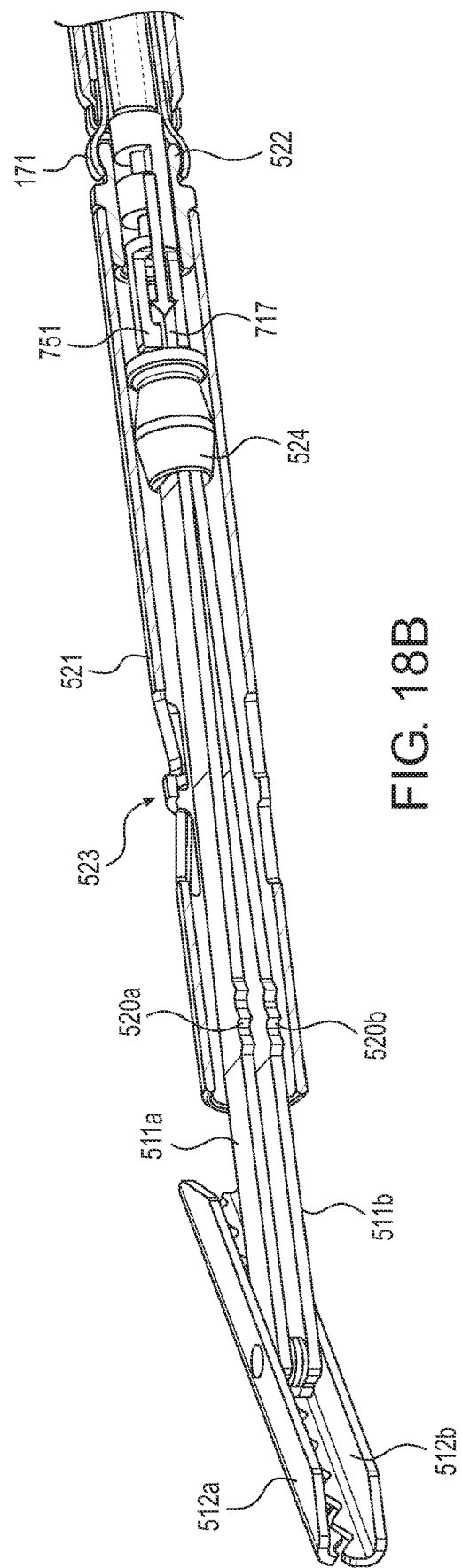
Figure 18E:
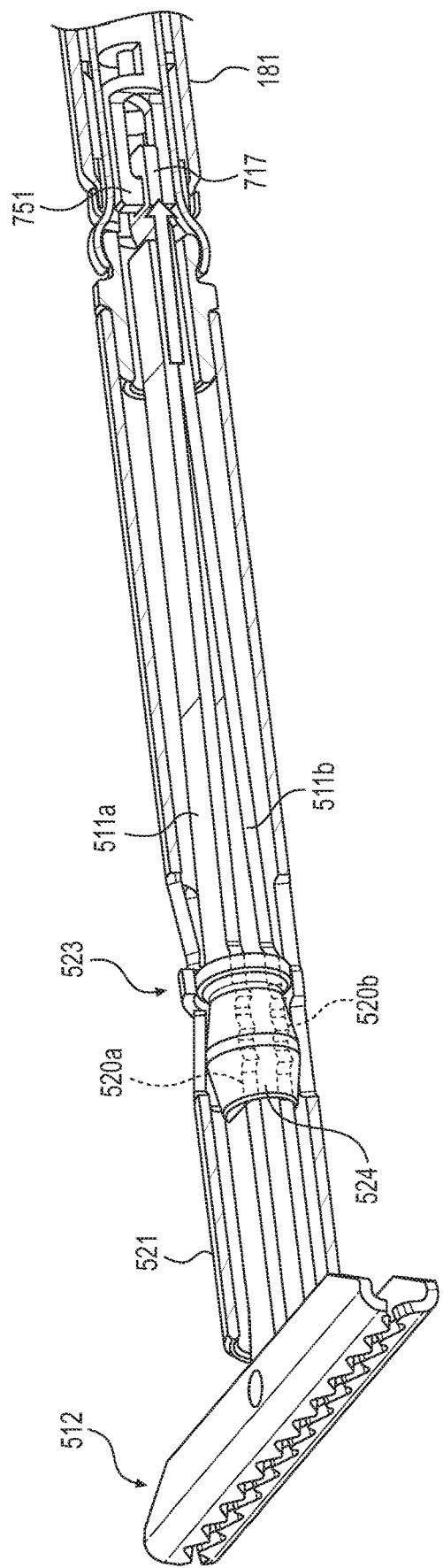

In FIG. 18A, the clip arms 511a, 511b are still disposed inside the channel of the lock tube 521 in the delivery configuration. In FIG. 18B, the jaws 512a, 512b have been liberated from the lock tube 521 and have started to rotate a small amount by spring action. Additionally, the locking slider 524 has been pushed by the fork connector 751 so as to advance in the distal direction. The clip 511 is retracted in the proximal direction in FIG. 18C such that the jaws 512 abut against the distal end of the lock tube 521 so that the jaws are fully pivoted with respect to the clip arms 511a, 511b. In FIG. 18D, the clip 511 is advanced in the distal direction to deploy the clip 511 in the open configuration for clipping tissue. The locking slider 524 has likewise been advanced in the distal direction (due to, for example, pushing by the fork connector 751 when the clip 511 is advanced) in FIG. 18D so as to be locked in place in the locking connector 523 in the lock tube 521. Then, the clip 511 shifted from the open configuration in FIG. 18D to the closed, tissue-clipping configuration shown in FIG. 18E. Then, the clip 511 is retracted in the proximal direction such that the locking teeth 520a, 520b on the clip arms 511a, 511b are lockingly engaged inside the slider 524 so as to lock the clip 511 to the lock tube 521 in the closed configuration. The locking mechanism shown in FIGS. 18A-18E can be used with any of the radial clip arm structures (e.g., 511 or 611) discussed above.

The illustrated exemplary embodiments of the apparatus and method as set forth above are intended to be illustrative and not limiting and can be combined. For example, the releasable clip connection structures may be combined with any of the various releasable lock tube connection structures. Similarly, the radial and jaw clip arm structures may be interchangeable. Various changes may be made without departing from the spirit and scope of the invention.

What is claimed is:

1. A tissue clipping device, comprising:
a lock tube having a channel extending therethrough from a distal end to a proximal end; and
a clip comprising clip arms coupled to each other at a proximal end, the clip being at least partially disposed within the channel of the lock tube and being configured to move distally and proximally relative to the lock tube between:
an open configuration in which distal ends of the clip arms are separated from each other for receiving tissue therebetween, and
a closed configuration in which the distal ends of the clip arms are closer to each other than in the open configuration for clipping the tissue received therebetween,
wherein:
the clip comprises a first connector configured to engage a second connector comprised by the lock tube to lock the clip in the closed configuration,
the first connector is disposed within the channel of the lock tube regardless of whether the clip is in the open configuration or the closed configuration, including when the clip is locked in the closed configuration, and
the second connector comprises a tab that is formed in a wall of the lock tube and is configured to: (i) expand radially outward under a force of the first connector passing through the second connector, and (ii) move radially inward after the first connector has passed through the tab to lock the clip to the lock tube.

2. The tissue clipping device according to claim 1, wherein the clip arms have outer surfaces free of protrusions.

3. The tissue clipping device according to claim 1, wherein the clip comprises more than two clip arms.

4. The tissue clipping device according to claim 1, wherein the first connector is fixed to the proximal end of the clip.

5. The tissue clipping device according to claim 1, wherein the clip comprises jaws pivotably coupled to the distal ends of the clip arms.

6. The tissue clipping device according to claim 5, wherein the jaws are configured to:
extend in a direction parallel to a longitudinal axis of the clip arms when the jaws are disposed inside the channel of the lock tube, and
pivot with respect to the clip arms when the jaws are exposed from the distal end of the lock tube.

7. The tissue clipping device according to claim 1, wherein the first connector is disposed within the channel of the lock tube so as to be slidable relative to the clip arms and the lock tube, and the first connector is configured to engage: (i) locking teeth formed on the clip arms, and (ii) the second connector to lock the clip in the closed configuration.

8. The tissue clipping device according to claim 1, wherein the lock tube includes a flexible portion.

9. A tissue clipping system comprising:
the tissue clipping device according to claim 1; and
a delivery device releasably coupled to the tissue clipping device, the delivery device comprising:
an insertion member having a channel extending therethrough from a distal end to a proximal end, the distal end of the insertion member being releasably coupled to the proximal end of the lock tube; and
a control member extending through the channel of the insertion member and having a distal end and a proximal end, the distal end of the control member being releasably coupled to the proximal end of the clip;
wherein the tissue clipping device is configured to be released from the delivery device after the clip is locked in the closed configuration.

10. The tissue clipping system according to claim 9, wherein:
the proximal end of the clip is releasably coupled to a hook connector formed on the distal end of the control member; and
the hook connector is configured to release the proximal end of the clip after the lock tube is released from the insertion member.

11. The tissue clipping system according to claim 9, wherein:
a fork connector is formed on the proximal end of the clip or the distal end of the control member to releasably couple the clip and control member; and
the fork connector configured to release the clip from the control member before the lock tube is released from the insertion member.

12. The tissue clipping system according to claim 9, wherein:
the proximal end of the lock tube is releasably coupled to the distal end of the insertion member via a ball and socket connection in which the distal end of the insertion member is held around the proximal end of the lock tube by a locking ring formed on a distal end of a sheath disposed around the insertion member; and the ball and socket connection is configured to be released by retracting the sheath.

13. The tissue clipping system according to claim 9, wherein the proximal end of the lock tube is releasably coupled to the distal end of the insertion member via a frictional connection between the lock tube and a connector slidably disposed within the distal end of the insertion member.

14. The tissue clipping system according to claim 9, wherein the proximal end of the lock tube is releasably coupled to a connector comprising wedge jaws disposed on the distal end of the insertion member.

15. The tissue clipping system according to claim 9, wherein:
the proximal end of the lock tube is releasably coupled to a break-away connector formed on the distal end of the insertion member; and
the lock tube is configured to be released from the insertion member by advancing the insertion member distally to break a breakable portion of the break-away connector.

16. The tissue clipping system according to claim 9, wherein:
the proximal end of the lock tube is releasably coupled to the distal end of the insertion member via a bendable sheet connector comprising a bendable sheet that extends through slots formed in the insertion member and the lock tube, the bendable sheet including an opening through which the control member extends; and
the lock tube is configured to be released from the insertion member by retracting the control member proximally such that a clip connector formed on the distal end of the control member abuts and deforms the bendable sheet.

17. The tissue clipping system according to claim 9, wherein the insertion member comprises a spiral tube.

18. A tissue clipping device comprising:
a lock tube having a channel extending therethrough from a distal end to a proximal end;
a clip comprising clip arms extending from distal ends to proximal ends through the channel of the lock tube, the clip arms being movable relative to the lock tube between an open configuration in which the clip arms are separated from each other and a closed configuration in which the clip arms are closer to each other than in the open configuration; and
jaws, each of which is pivotably coupled to a respective distal end of a corresponding one of the clip arms, wherein:
the jaws are configured to:
extend in a direction such that longitudinal axes of the jaws are substantially aligned with longitudinal axes of the clip arms when the jaws are disposed inside the channel of the lock tube, and
pivot with respect to the clip arms so as to extend in a direction transverse to the longitudinal axes of the clip arms when the jaws are exposed from the distal end of the lock tube,
the clip comprises a first connector configured to engage a second connector comprised by the lock tube to lock the clip in the closed configuration, and
the first connector is slidably disposed within the channel of the lock tube and is configured to engage: (i) locking teeth formed on the clip arms, and (ii) the second connector to lock the clip in the closed configuration.

19. The tissue clipping device according to claim 18, wherein the jaws are configured to pivot with respect to the clip arms so as to extend in a direction substantially orthogonal to the longitudinal axes of the clip arms.

20. The tissue clipping device according to claim 18, wherein the jaws further comprise a control wire configured to pivot the jaws with respect to the clip arms as the clip arms are advanced distally relative to the lock tube.

21. The tissue clipping device according to claim 18, wherein the jaws comprise a bump configured to create a preload for pivoting the jaws.

22. The tissue clipping device according to claim 18, wherein the lock tube includes a flexible portion.

23. The tissue clipping device according to claim 18, wherein:
the clip arms include a first portion having a first width and a second portion having a second width that is smaller than the first width, the first width and the second width extending a direction orthogonal to the longitudinal axes of the clip arms and orthogonal to an opening direction of the clip arms in the open configuration, and
the jaws are configured to pivot with respect to the clip arms due to preload received from the first portion.

24. A method for clipping tissue comprising:
inserting a tissue clipping device into a body, the clipping device comprising a clip including clip arms coupled to each other at a proximal end, and a lock tube at least partially housing the clip in a channel formed therein;
advancing the clip distally out of a distal end of the lock tube so that the clip arms separate from each other in a radial direction to form an open configuration for receiving tissue;
positioning the clip such that distal ends of the clip arms are adjacent to a portion of tissue surrounding a tissue opening to be closed; and
advancing the lock tube distally relative to the clip such that:
the clip arms are contracted toward each other in a radial direction to form a closed configuration for clipping the tissue received between the clip arms; and
a first connector comprised by the clip engages a second connector comprised by the lock tube to lock the clip in the closed configuration,
wherein:
the first connector is disposed within the channel of the lock tube regardless of whether the clip is in the open configuration or the closed configuration,
the second connector comprises a tab formed in a wall of the lock tube, and
when the first connector engages the second connector to lock the lip in the closed configuration, the tab expands radially outward under a force of the first connector passing through the second connector, and then moves radially inward after the first connector has passed through the tab to lock the clip to the lock tube.

25. The method according to claim 24, the lock tube includes a flexible portion formed by laser processing.

* * * * *